(12) United States Patent
DeNise et al.

(10) Patent No.: US 7,468,248 B2
(45) Date of Patent: Dec. 23, 2008

(54) METHODS AND SYSTEMS FOR INFERRING BOVINE TRAITS

(75) Inventors: Sue K. DeNise, Davis, CA (US); Richard Kerr, Davis, CA (US); David Rosenfeld, Sacramento, CA (US); Tom Holm, Salt Lake City, UT (US); Stephen Bates, Davis, CA (US); Dennis Fantin, Danville, CA (US)

(73) Assignees: Cargill, Incorporated, Wayzata, MN (US); MMI Genomics, Inc., Beltsville, MD (US)

( * ) Notice: Subject to any disclaimer, the term of this patent is extended or adjusted under 35 U.S.C. 154(b) by 295 days.

(21) Appl. No.: 10/750,623

(22) Filed: Dec. 31, 2003

(65) Prior Publication Data

US 2005/0287531 A1 Dec. 29, 2005

Related U.S. Application Data

(60) Provisional application No. 60/437,482, filed on Dec. 31, 2002.

(51) Int. Cl.
*C12Q 1/68* (2006.01)
*C12P 19/34* (2006.01)

(52) U.S. Cl. .......................................... 435/6; 435/91.2

(58) Field of Classification Search ........................ None
See application file for complete search history.

(56) References Cited

U.S. PATENT DOCUMENTS

| | | | |
|---|---|---|---|
| 5,582,987 A | 12/1996 | Lewin et al. | |
| 5,612,179 A | 3/1997 | Simons | |
| 5,851,762 A | 12/1998 | Simons | |
| 6,103,446 A | 8/2000 | Devlin et al. | |
| 6,218,119 B1 | 4/2001 | Kuiper et al. | |
| 6,242,191 B1 | 6/2001 | Fluharty et al. | 435/6 |
| 6,383,751 B1 | 5/2002 | Barendse | |
| 6,410,231 B1 | 6/2002 | Arnold et al. | 435/6 |
| 6,458,531 B1 | 10/2002 | Rothschild et al. | |
| 6,458,544 B1 | 10/2002 | Miller | 435/6 |
| 6,701,869 B2 | 3/2004 | Fuqua | |
| 2002/0012934 A1 | 1/2002 | Meghen et al. | 435/6 |
| 2002/0098534 A1 | 7/2002 | McCaskey-Feazel et al. | 435/19 |
| 2002/0107211 A1 | 8/2002 | Friedman et al. | |
| 2002/0119442 A1 | 8/2002 | Dunlop et al. | |
| 2002/0123058 A1 | 9/2002 | Threadgill et al. | |
| 2002/0137139 A1 | 9/2002 | Byatt et al. | |
| 2002/0137160 A1 | 9/2002 | Byatt et al. | |
| 2003/0009292 A1 | 1/2003 | Mei et al. | 702/19 |
| 2003/0017487 A1 | 1/2003 | Xue et al. | 435/6 |
| 2003/0104424 A1 | 6/2003 | Tuggle et al. | |
| 2003/0129609 A1 | 7/2003 | Tuggle et al. | |
| 2003/0190644 A1 | 10/2003 | Braun et al. | |
| 2003/0219819 A1 | 11/2003 | Marquess | |
| 2004/0018511 A1* | 1/2004 | Cai et al. | 435/6 |

FOREIGN PATENT DOCUMENTS

| | | |
|---|---|---|
| EP | 1 256 632 | 2/2002 |
| EP | 0566 793 | 4/2002 |
| FR | 2 779 153 | 5/1999 |
| WO | WO92/13102 | 8/1992 |
| WO | WO95/15400 | 6/1995 |
| WO | WO98/39475 | 9/1998 |
| WO | WO99/01576 | 1/1999 |
| WO | WO00/36143 | 6/2000 |
| WO | WO00/69882 | 11/2000 |
| WO | WO01/21801 A1 | 3/2001 |
| WO | WO01/67211 | 9/2001 |
| WO | WO01/75161 | 10/2001 |
| WO | WO01/92570 | 12/2001 |
| WO | WO02/02822 | 1/2002 |
| WO | WO02/36824 | 5/2002 |
| WO | WO02/38737 | 5/2002 |
| WO | WO02/40709 A2 | 5/2002 |

(Continued)

OTHER PUBLICATIONS

Ioannidis et al. Replication validity of genetic association studies. Nature Genetics (2001) 29:306-309.*

(Continued)

*Primary Examiner*—Kenneth R. Horlick
*Assistant Examiner*—David C Thomas
(74) *Attorney, Agent, or Firm*—King & Spalding LLP

(57) ABSTRACT

Methods, compositions, and systems are provided for managing bovine subjects in order to maximize their individual potential performance and edible meat value, and to maximize profits obtained in marketing the bovine subjects. The methods and systems draw an inference of a trait of a bovine subject by determining the nucleotide occurrence of at least one bovine SNP that is identified herein as being associated with the trait. The inference is used in methods of the present invention to establish the economic value of a bovine subject, to improve profits related to selling beef from a bovine subject; to manage bovine subjects, to sort bovine subjects; to improve the genetics of a bovine population by selecting and breeding of bovine subjects, to clone a bovine subject with a specific trait, to track meat or another commercial product of a bovine subject; and to diagnose a health condition of a bovine subject. Methods are also disclosed for identifying additional SNPs associated with a trait, by using the associated SNPs identified herein.

33 Claims, No Drawings

FOREIGN PATENT DOCUMENTS

| WO | WO02/009510 A2 | 7/2002 |
| --- | --- | --- |
| WO | WO02/059374 A1 | 8/2002 |
| WO | WO02/064749 A2 | 8/2002 |
| WO | WO02/064820 | 8/2002 |
| WO | WO02/072871 A2 | 9/2002 |
| WO | WO02/076190 A2 | 10/2002 |
| WO | WO02/090569 | 11/2002 |
| WO | WO02/090589 | 11/2002 |
| WO | WO2004/013346 A2 | 2/2004 |

OTHER PUBLICATIONS

Heaton et al. Selection and use of SNP markers for animal identification and paternity analysis in U.S. beef cattle. Mammal. Genome (2002) 13:272-281.*

Akhter et al. Bos taurus clone RP42-360C18. GenBank Accession No. AC092085 (2002).*

Lucentini, Jack, "Reproducible Gene-Disease Associations are Few and Far Between", *The Scientist*, vol. 18, 2004.

Wacholder, Shalom et al., "Asssessing the Probability That a Positive Report is False: An Approach for Molecular Epidemiology Studies", *J. Natl. Cancer Institute*, vol. 96, pp. 434-442, 2004.

Zhang, H.M., et al., "Rapid Communication: A Novel DNA Polymorphism of the Bovine Calpain Gene Detected by PCR-RFLP Analysis"; J. Anim. Sci. 1996; 74:1441.

Davis, G.P., et al., "The Impact of Genetic Markers on Selection", J. Anim. Sci 1998, 76:2331-2339.

Denise, S.K., et al., "Genetic Parameter Estimates for Postweaning Traits of Beef Cattle in a Stressful Environment", J. Anim. Sci. 1989, 67:2619-2626.

Du, F.X., et al., "Heterozygosity for Genes Influencing a Quantitative Trait", J. Anim. Sci. 2002, 80:1478-1488.

Unanian, M.M., et al., "Rapid Communication: Polymerase Chain Reaction-Restriction Fragment Length Polymorphism in the Bovine Growth Hormone Gene", J. Anim. Sci. 1994, 72:2203.

Zhang, H.M., et al., "Rapid Communication: Polymerase Chain Reaction-Restriction Fragment Length Polymorphism Analysis of the Bovine Somatotropin Gene", J. Anim. Sci. 1993, 71:2276.

Zhang, H.M., et al., "Rapid Communication: Diallelic Single-Stranded Conformational Polymorphism Detected in the Bovine Prolactin Gene", J. Anim. Sci. 1994, 72:256.

Ax, R.L., et al. "New developments in managing the bull: Factors Affecting Calf Corp: Biotechnology of Reproduction", CRC Press, 2001.

Denise, S.K., et al., "Genetic Technologies: Factors Affecting Calf Corp: Biotechnology of Reproduction", CRC Press, 2002.

Denise, R.S.K., et al. "Genetic and environmental aspects of the growth curve parameters in beef cows", J. Anim. Sci. 1985, 61:1431.

Denise, R.S.K., et al., "Relationships among postweaning weights and gains of cattle raised under range and gain test environments", J. Anim. Sci. 1987, 64:969.

Denise, R.S.K., et al., "Relationships among udder shape, udder capacity, cow longevity and calf weights", J. Anim. Sci. 1987, 65:366.

Tanida, H., et al., "Genetic aspects of longevity in Angus and Hereford cows", J. Anim. Sci. 1988, 66:640.

Zhang, H.M., et al., "Nucleotide sequence determination of a bovine somatotropin allele", An. Genetics., 1992, 23:578.

Lagziel, A., et al., "Geographic and breed distribution of an MspI PCR-RFLP in the bovine growth hormone (bGH) gene", Anim.. Genet. 2000, 31:210-213.

Denise, S.K., et al., "The use of genetic markers in dairy and beef cattle improvement: Proc. Southwest Nutr. And Manage", Conf., Tempe, AZ 1993.

Denise, S.K., et al., "Genetic screening for disease and production: Proc. Western Canadian Dairy Sem.", Red Deer, Alberta 1993.

Denise, S.K., et al., "Incorporation of molecular genetic information into genetic prediction models: Proc. Genetic Prediction Workshop, Beef Improvement Federation", Kansas City, Jan. 1994.

Denise, S.K., et al., "Gene mapping, marker-assisted selection, QTLs-Boiling it down to cowboy lingo. Proc. Beef Improvement Federation Annual Meeting", Des Moines, Iowa, Jun. 1994.

Denise, S.K., "Biotechnology and Animal Breeding: What can we use today and what does the future hold?" Great Plains Beef Cattle Handbook 1994.

* cited by examiner

METHODS AND SYSTEMS FOR INFERRING BOVINE TRAITS

CROSS REFERENCE TO RELATED APPLICATION

This application claims the benefit of priority under 35 U.S.C. § 119(e) of U.S. Ser. No. 60/437,482, filed Dec. 31, 2002, the entire content of which is incorporated herein by reference.

BACKGROUND OF THE INVENTION

1. Field of the Invention

The specification hereby incorporates by reference in their entirety under 37 C.F.R. § 1.77(b)(4), the files contained on the three compact discs filed herewith. The first and second compact discs each includes a file entitled "mmi1 100-1 Table 1A.txt," created Sep. 23, 2004, which is 8,960 kilobytes in size, and a file entitled "mmi1 100-1 Table 1B.txt," created Sep. 23, 2004, which is 11,817 kilobytes in size. The first and second compact discs are duplicates as required under 37 C.F.R. § 1.52(e)(4). The third compact disc includes a file entitled "MMI1 100-1. txt," created Sep. 22, 2004, which is 88,025 kilobytes in size.

The invention relates generally to gene association analyses and more specifically to polymorphisms and associated traits of bovine species.

2. Background Information

Under the current standards established by the United States Department of Agriculture (USDA), beef from bulls, steers, and heifers is classified into eight different quality grades. Beginning with the highest and continuing to the lowest, the eight quality grades are prime, choice, select, standard, commercial, utility, cutter and canner. The characteristics which are used to classify beef include age, color, texture, firmness, and marbling, a term which is used to describe the relative amount of intramuscular fat of the beef. Well-marbled beef from bulls, steers, and heifers, i.e., beef that contains substantial amounts of intramuscular fat relative to muscle, tends to be classified as prime or choice; whereas, beef that is not marbled tends to be classified as select. Beef of a higher quality grade is typically sold at higher prices than a lower grade beef. For example, beef that is classified as "prime" or "choice," typically, is sold at higher prices than beef that is classified into the lower quality grades.

Classification of beef into different quality grades occurs at the packing facility and involves visual inspection of the ribeye on a beef carcass that has been cut between the 12th and 13th rib prior to grading. However, the visual appraisal of a beef carcass cannot occur until the animal is harvested. Ultrasound can be used to give an indication of marbling prior to slaughter, but accuracy is low if ultrasound is done at a time significantly prior to harvest.

Currently there are no cost effective methods for identifying live cattle that give accurate prediction of the genetic potential to produce beef that is well-marbled. Such information could be used by feedlot operators to identify animals for purchase prior to finishing, to identify animals under contract for one or more premium programs administered by a packer, by feedlot managers to make management decisions regarding individual animals within a lot (including nutrition programs and sale dates), by cow-calf producers in marketing their animals to various feedlots or in making decisions regarding which animals will be sold on various carcass evaluation grids. Such information could also be used to identify cattle that are good candidates for breeding. Thus, it is desirable to have a method which can be used to assess the beef marbling potential of live cattle, particularly young cattle well in advance of the arrival of the animal at the packing house.

Another characteristic of beef that is desired by consumers is tenderness of the cooked product. Currently there are no procedures for identifying live animals whose beef, if cooked properly, would be tender. Currently, there are two types of procedures which are used by researchers to assess the tenderness of meat samples after they have been aged and subsequently cooked. The first involves a subjective analysis by a panel of trained testers. The second type is characterized by methods used to cut or shear meat samples that have been removed from an animal and aged. One such method is the Warner-Bratzler shear force procedure which involves an instrumental measurement of the force required to shear core samples of whole muscle after cooking. Neither of these procedures can be used to any practical effect in a fabrication setting as the need to age product prior to testing would lead to maintenance of inventory of fabricated product that would be cost prohibitive. Consequently, the methods are used at research facilities but not at packing plants. Accordingly, it is desirable to have new methods which can be used to identify carcasses and live cattle that have the potential to provide beef that, if cooked properly, will be tender.

It has been difficult for the livestock industry to combine genetics for red meat yield and marbling and/or tenderness. In fact, conventional measurement techniques indicate that marbling and red meat yield tend to be antagonistic. Hence, there is a need for tools that identify superior genetic potential for the combination of red meat yield, tenderness and marbling. Another trait of interest is live cattle growth rate (average daily gain). Currently, cattle producers do not have tools to identify animals with superior genetic potential for rapid growth prior to purchase. In addition, there are no methods currently available to identify animals which combine capability for superior growth rate with desirable carcass characteristics.

While many methods of measurement and selection of cattle in feedlots have been tried, both visual and automated, such as ultrasound, none have been successful in accomplishing the desired end result. That end result is the ability to identify and select cattle with superior genetic potential for desirable characteristics and then manage a given animal with known genetic potential for shipment at the optimum time, considering the animal's condition, performance and market factors, the ability to grow the animal to its optimum individual potential of physical and economic performance, and the ability to record and preserve each animal's performance history in the feedlot and carcass data from the packing plant for use in cultivating and managing current and future animals for meat production. The beef industry is extremely concerned with its decreasing market share relative to pork and poultry. Yet to date, it has been unable to devise a system or method to accomplish on a large scale what is needed to manage the current diversity of cattle (i.e. least about 100 different breeds and co-mingled breeds) to improve the beef product quality and uniformity fast enough to remain competitive in the race for the consumer dollar spent on meat.

Modern day breeding programs in animal agriculture originated from fundamental observations made upon the first domestication of animals. Early humans observed differences in a broad range of characteristics between the offspring produced by mating different parents and they took advantage of this observation by only mating individuals that demonstrated the most desirable characteristics. By following this strategy for several generations our ancestors were able to create populations of animals that exhibited only desirable traits that best fit their needs. This strategy, called selective mating or selective breeding, is based on identifying the best progeny from one generation and making them the parents for the next generation. Selective breeding results in the development of individuals that are superior for one or more traits and is the backbone for modern day genetic improvement programs in animal agriculture.

Through the utilization of selective breeding strategies geneticists have been able to define the fundamental genetic parameters that influence the expression of traits. Breeding experiments revealed that some traits, like coat color, were expressed in a qualitative manner and could be easily passed onto the next generation while other traits, like growth rate or adult size, were expressed in a quantitative fashion and only small progress could be made at each generation. Subsequent research in the field of molecular genetics has now revealed that qualitative trait effects are caused by the action of a single gene while quantitative traits are caused by the action and interaction of many different genes.

In addition to contributions of genetics, it has been determined that genetic source alone did not account for all of the differences observed among groups of closely related individuals and that environment and management also played a role in determining the expression of specific traits. In order to account for all of the differences observed between individuals for a specific trait geneticists developed the equation; P (phenotype or overall trait expression)=G (genetic contribution from parents)+E (contribution from the environment). Geneticists observed that some traits respond better to selection than others due to intrinsic differences in G and E and developed scientific methods for determining the genetic contribution, or heritability, for a number of unique traits. For any given trait a higher heritability indicates more of the total variation is accounted for by the genetic source and a faster response to selection can be achieved. The parameters that govern differences in the expression of specific traits between individuals as defined above have been used for decades to make genetic improvement in animal agriculture production. Utilization of these parameters in a "Classical Breeding Program" provides breeders with a set of tools to evaluate the genetic makeup of different individuals within a population and to make steady progress in improving the expression of traits that have economic significance to the commercial production of livestock species.

The primary objective of any genetic improvement program is to ascertain the genetic potential of individuals for a broad range of economically important traits at a very early age. While the classical breeding approach has produced steady genetic improvement in livestock species it is limited by the fact that accurate prediction of an individual's genetic potential can only be achieved when the animal reaches adulthood (fertility and production traits) or is harvested (meat quality traits). This is particularly problematic for meat animals since harvested animals obviously cannot enter the breeding pool. Furthermore, it is difficult to utilize the classical breeding approach for traits that are difficult (disease resistance) or costly (meat tenderness) to measure.

To overcome the previous problems with the classical breeding approach animal breeders and geneticists turned to the new fields of molecular genetics and genomics. These disciplines offered the promise that the underlying genes responsible for genetic variation of important traits could be identified. Targeted research programs were initiated to ascertain the location and functional differences of specific genes that contribute to genetic variation for defined traits. The primary goal of molecular breeding programs in livestock species is to develop genetic assays for economically important traits that can be tested on individual animals at an early age, can be used for traits that are difficult to measure, that provide an accurate estimate of an animals genetic potential for expression of the trait, and account for a large proportion of the total genetic variation observed for the trait in commercial populations.

To date, three different experimental approaches have been utilized to identify genes that effect economically important traits in livestock species: Candidate Gene Approach, Differential Gene Expression Approach, and Within Family Quantitative Trait Loci (QTL) Linkage Approach. Limited success has been achieved for each of these methods in identifying genes that contribute to genetic variation for defined traits. However, each method also has limitations, as the primary objectives of the molecular breeding approach described above have not been achieved. Accordingly, a need exists for methods that assist in a determination of the genetic potential of individuals for a broad range of economically important traits at a very early age. A description of each of the experimental approaches attempted thus far, and the limitations for each is outlined below:

In the candidate gene approach a specific gene or set of genes is targeted based on the hypothesis they may have an effect on a particular trait. The hypothesis is developed based on existing information of biochemical pathways and the function of the gene in another species, most often human or mouse where substantial gene characterization has been performed. The known sequence of the human or mouse gene is used to fish-out the gene in the target species. The DNA sequence of the gene in the target species is determined by sequencing a large number of individuals and any sequence variation is cataloged. The sequence variations are developed into diagnostic assays and genotyped against a population of animals where phenotypic variation for the targeted traits has been characterized. The data set is analyzed to determine if statistically significant associations exist between specific sequence variants and expression of the trait.

The candidate gene approach has been successful in identifying genes and sequence variants that have an effect on a particular trait. However, this approach does have limitations and is analogous to finding a needle-in-the-haystack. With over 30,000 genes characterized in humans and mouse as a result of the whole genome sequence the first difficulty is identifying a gene that will actually contribute to genetic variation for a specific trait. Secondly, a large enough set of individuals must be sequenced to find the sequence variant that is responsible for or at least highly associated with the effect. And finally, if an effect is present at all the population of animals screened must be large enough to ensure statistically significant association of the effect. While it is feasible to meet all of these conditions to discover significant associations the cost of this approach is high because it is a random method that cannot be targeted to genes that have the largest effect.

In the differential gene expression approach, differences in gene expression are characterized for specific genes and in targeted tissues with the hope of identifying genes that may be contributing to the observed genetic variation for a particular trait. As in the Candidate Gene Approach, targeted genes and tissues are chosen based on existing information of biochemical pathways and the functions of genes in other species. Differential gene expression has been effective in identifying genes that are turned on or off by extreme differences in environment or by disease, but has been less successful in identifying genes that contribute to phenotypic variation in livestock production traits. Current technology platforms for detecting differences in gene expression require large differences in gene expression, often up to a 2 to 3 fold increase or decrease. Gene expression differences that may account for genetic variation in livestock traits may be under the detection threshold for existing gene expression technology.

Differential gene expression technology has been successfully used to elucidate biochemical pathways and to understand basic cellular functions but has not demonstrated any utility in the development of diagnostic assays to predict genetic potential of animals for specific traits. Even if differential expression of a gene is observed and can be directly attributed to phenotypic variation for a trait there is no guarantee that a sequence variant can be found in the gene or that the sequence variant is responsible for the effect. In many situations sequence variants for differentially expressed genes do not association with the observed difference in phenotypes. This could be explained by the action of other genes or gene products that regulate the expression of the differentially expressed gene but are located elsewhere in the genome.

In the within-family QTL linkage approach, small families of related individuals are bred-up or assembled, DNA samples are taken from all individuals in the population, phenotypic measurements for the targeted traits are taken on the progeny and a set of polymorphic DNA markers that span the genome are genotyped against the entire research population. The data set is then analyzed to determine if a particular marker or a linked set of markers have specific allele(s) that predominately associate with the phenotypic variation observed in the progeny from a specific parent or set of parents. A large number of research reports claiming linkage between specific traits and markers have been published for a wide variety of traits and in several different livestock species.

Although the within family QTL linkage approach has resulted in a number of reported linkages between targeted traits and specific marker locations this approach does not result in the direct development of diagnostic assays that can predict an animals genetic potential for the targeted trait. In practice, the research populations used for these experiments are very small, often only representing two or three different sire families, and as such, they do not represent the broad pattern of genetic variation that is observed across commercial animal populations. These small research populations are also problematic because the QTL can only be identified when it is heterozygous for a particular family group. Linkages between a marker and a trait are determined by allele frequency differences in the marker between progeny separated into groups with high versus low expression for the trait. This implies that the QTL itself must be heterozygous in order to be detected and the smaller the population the less likely it is to find QTLs in a heterozygous state. Furthermore, research populations designed to identify linkages in livestock species are usually half-sib designs where it is only possible to measure the genetic variation contributed by the male side of the pedigree. Half-sib designs have limited effectiveness in discovering significant linkages because only one-half of the genetic variation is accounted for in the analysis. Finally, the research populations are often comprised of animals and/or breed types that have extreme phenotypic differences for the targeted traits to insure the discovery of markers that demonstrate linkage to the trait. These extreme phenotypic crosses do not represent mainstream industry breeding practices and therefore, any reported linkage is suspect because it may only exist as an artifact within the research population and may not actually be segregating in commercial animal breeding populations.

Another limitation of the within family QTL approach is the lack of marker density for the linkage map used in the study. Due to cost and genotyping throughput issues all reported QTL linkage studies performed to date in livestock species have only used 100 to 200 total markers to cover the entire genome. With such a limited number of markers it is impossible to pinpoint the exact location of the QTL on the chromosome. Linkage distances ranging from 3 to over 60 centi-Morgans are commonly reported between the QTL and the linked marker(s). These broad linkage groups can actually span an entire chromosome and contain thousands of genes that are possible candidates for the observed effect. Because of these large distances, recombination between homologous chromosomes does not allow the use of linked markers identified in research populations to be used as predictors of genetic potential in commercial animal populations. Markers linked to QTLs can provide clues about the potential location of genes that have effects for certain traits but substantial additional research and validation is required to accurately pinpoint the location of the gene responsible for the effect and develop diagnostic assays to predict the expression of the trait.

In summary, three different experimental approaches have been used with limited success to identify genes, chromosomal regions or DNA markers that account for a large proportion of the genetic variation observed in economically important traits in livestock species. The results achieved from research programs utilizing these methods have not been widely utilized to date because they do not account for enough of the total genetic variation to allow accurate prediction of an animal's performance for a specific trait. Furthermore, even when successful these approaches are only capable of identifying additive genetic components while ignoring non-additive genetic components such as dominance (i.e. dominating trait of an allele of one gene over an allele of a another gene) and epistasis (i.e. interaction between genes at different loci) which are critical to the development of diagnostics that can be utilized by animal breeders to accurately predict genetic potential for economically important traits in livestock species.

SUMMARY OF THE INVENTION

The present invention provides methods, systems, and compositions that allow the identification and selection of cattle with superior genetic potential for desirable characteristics. Accordingly, the present invention provides methods, compositions, and systems for managing, selecting and mating, breeding, and cloning cattle. These methods for identification and monitoring of key characteristics of individual animals and management of individual animals maximize their individual potential performance and edible meat value. The methods of the invention provide systems to collect, record and store such data by individual animal identification so that it is usable to improve future animals bred by the producer and managed by the feedlot. The methods, compositions, and systems provided herein utilize information regarding genetic diversity among cattle, particularly single nucleotide polymorphisms (SNPs), and the effect of nucleotide occurrences of SNPs on important traits.

The present invention further provides methods for selecting a given animal for shipment at the optimum time, considering the animal's genetic potential, performance and market factors, the ability to grow the animal to its optimum individual potential of physical and economic performance, and the ability to record and preserve each animal's performance history in the feedlot and carcass data from the packing plant for use in cultivating and managing current and future animals for meat production. These methods allow management of the current diversity of cattle to improve the beef product quality and uniformity, thus improving revenue generated from beef sales.

This invention allows the identification of animals that have superior traits that can be used to identify parents of the next generation through selection. These methods can be imposed at the nucleus or elite breeding level where the improved traits would, through time, flow to the entire population of animals, or could be implemented at the multiplier or foundation parent level to sort parents into most genetically desirable. The optimum male and female parent can then be identified to maximize the genetic components of dominance and epistasis, thus maximizing heterosis and hybrid vigor in the market animals.

In one embodiment, the present invention provides an isolated polynucleotide that includes at least 20 contiguous nucleotides of any one of SEQ ID NOS:24493 to 64886, a polynucleotide at least 90% identical to the 20 contiguous nucleotide fragment, or a complement thereof, wherein the isolated polynucleotide includes a nucleotide occurrence of a single nucleotide polymorphism (SNP) associated with a trait, wherein the SNP corresponds to position 300 of SEQ ID NOS:19473 to 21982.

In another embodiment, the invention provides methods to draw an inference of a trait of a bovine subject by determining the nucleotide occurrence of at least one bovine SNP that is determined using methods disclosed herein, to be associated with the trait. For example, the inference can be drawn by determining the nucleotide occurrence of at least one SNP identified in Tables 1A and 1B (i.e. a SNP corresponding to position 300 of SEQ ID NOS:19473 to 21982). The inference can be drawn regarding, for example, fat thickness, retail yield, marbling, tenderness, or average daily gain.

The inference is used in methods of the present invention for the following aspects of the invention: to establish the economic value of a bovine subject; to improve profits related to selling beef from a bovine subject; to manage bovine subjects; to sort bovine subjects; to improve the genetics of a bovine population by selecting and breeding of bovine subjects; to clone a bovine subject with a specific trait, a combination of traits, or a combination of SNP markers that predict a trait; to track meat or another commercial product of a bovine subject; to certify and brand a specific product based on known characteristics; and to diagnose a health condition of a bovine subject.

In another embodiment, the present invention provides a method for identifying a bovine target sequence, such as a gene, associated with a trait, by identifying an open reading frame present in a target region of the bovine genome, wherein the target region is located on the bovine genome less than or equal to about 500,000 nucleotides of a single nucleotide polymorphism (SNP) corresponding to position 300 of any one of SEQ ID NOS:19473 to 21982, and analyzing the open reading frame to determine whether it affects the trait, thereby identifying a bovine gene associated with the trait. In one aspect, the target region is located within about 5000 nucleotides of a single nucleotide polymorphism (SNP) corresponding to position 300 of any one of SEQ ID NOS:19473 to 21982.

In another embodiment, the present invention provides a method for identifying a bovine single nucleotide polymorphism (SNP) associated with a trait, that includes identifying a test SNP in a target region of a bovine genome, wherein the target region is less than or equal to about 500,000 nucleotides of a SNP position corresponding to position 300 of one of SEQ ID NOS:19473 to 21982, and identifying an association of the test SNP to the trait, thereby identifying the test SNP as associated with the trait. In certain aspects, the target region includes at least 20 contiguous nucleotides of SEQ ID NOS: 24493 to 64886. In another aspect, for example, the target region includes at least 20 contiguous nucleotides of SEQ ID NOS:19473 to 21982. The present invention also provides isolated polynucleotides that include the identified SNPs.

DETAILED DESCRIPTION OF THE INVENTION

The specification hereby incorporates by reference in their entirety, the files contained on the two compact discs filed herewith. Two copies of each of the two compact discs are filed herewith. The first compact disc includes a file called "MMI1 100-1 Table 1A.doc," created Dec. 31, 2003, which is 11299 kilobytes in size, and a file called "MMI1 100-1 Table 1B.doc," created Dec. 31, 2003, which is 11266 kilobytes in size. The Second disc includes a sequence listing which is included in a file called "MMI1 100-1 SEQUENCE LISTING.txt," created Dec. 31, 2003, which is 4770 kilobytes in size.

The compositions, methods, and systems of the invention are particularly well suited for managing, selecting or mating bovine subjects. They allow for the ability to identify and monitor key characteristics of individual animals and manage those individual animals to maximize their individual potential performance and edible meat value. Therefore, the methods, systems, and compositions provided herein allow the identification and selection of cattle with superior genetic potential for desirable characteristics.

The compositions, methods, and systems of the present invention are especially well-suited for implementation in a feedlot environment. They allow for the ability to identify and monitor key characteristics of individual animals and manage those individual animals to maximize their individual potential performance and edible meat value. Furthermore, the invention provides systems to collect, record and store such data by individual animal identification so that it is usable to improve future animals bred by the producer and managed by the feedlot. The systems can utilize computer models to analyze information regarding nucleotide occurrences of SNPs and their association with traits, to predict an economic value for a bovine subject.

Presently, feedlots contain pens which typically have a capacity of about 200 animals, and market to packers, pens of cattle that are fed to an average endpoint. The endpoint is calculated as a number of days on feed estimated from biological type, sex, weight, and frame score. Animals are initially sorted to a pen based on the estimated number of days on feed and incoming group. However, sorting is done by a series of subjective and suboptimal parameters, as discussed herein. The cattle are fed to an endpoint in order to maximize the percentage of animals from which Grade USDA Choice beef can be obtained at slaughter without developing cattle that are too fat, and thus get discounted for insufficient red meat yield. The present invention provides a method for maximizing a physical characteristic of a bovine subject, including optimizing the percentage of bovine subjects that produce Grade USDA Choice and Prime beef in the most efficient manner.

In one embodiment, the present invention provides an isolated polynucleotide that includes a fragment of at least 20 contiguous nucleotides of the bovine genome, or a complement thereof, wherein the isolated polynucleotide includes a nucleotide occurrence of a single nucleotide polymorphism (SNP) associated with a trait, wherein the SNP is in disequilibrium with a SNP corresponding to position 300 of any one of SEQ ID NOS:19473 to 21982. In certain aspects, the polynucleotide is located about 500,000 or less nucleotides from position 300 of SEQ ID NOS:19473 to 21982 on the bovine genome. As disclosed in the Examples herein, the linkage disequilibrium for cattle is about 500,000 nucleotides. Therefore, it is expected that other SNPs can be identified that are associated with the same traits based on the fact that these other SNPs are located less than or equal to about 500,000 nucleotides of the identified associated SNP on the bovine genome. In certain aspects, the polynucleotide is from an Angus, Charolais, Limousin, Hereford, Brahman, Simmental or Gelbvieh bovine subject.

The attached sequence listing provides sequences of contigs (SEQ ID NOS:24493 to 64886) generated from the bovine genome. It will be understood that contigs can be aligned such that SNPs that are on separate contigs, but are located within 500,000 nucleotides on the bovine genome, can be identified. For example, alignment of contigs and determination of distance between contigs provided herein, can be accomplished by using the sequence information of the human genome as a scaffold. Tables 1A and 1B (filed herewith on the compact disc), lists contigs that are "nearby" (i.e. within 500,000 nucleotides on the bovine genome) an associated SNP.

In certain aspects, the isolated polynucleotide includes a nucleotide corresponding to an associated SNP. Accordingly, in these aspects the isolated polynucleotide includes a nucleotide corresponding to position 300 of any one of SEQ ID NOS:19473 to 21982.

In another aspect, the present invention provides an isolated polynucleotide that includes a polynucleotide that is at least 20 nucleotides in length and is at least 90% identical to a fragment of at least 20 contiguous nucleotides of a bovine genome; or a complement thereof, wherein the fragment of at least 20 contiguous nucleotides of the bovine genome comprises a nucleotide occurrence of a single nucleotide polymorphism (SNP) associated with a trait, wherein the SNP is about 500,000 or less nucleotides from position 300 of any one of SEQ ID NOS:19473 to 21982. In certain aspects, for example, the polynucleotide is at least 90% identical to a fragment of at least 10, 15, 20, 25, 50, or 100 contiguous nucleotides of SEQ ID NOS:19473 to 21982. In certain aspects, the polynucleotide comprises position 300 of SEQ ID NOS:19473 to 21982.

As used herein, "about" means within ten percent of a value. For example, "about 100" would mean a value between 90 and 110.

In certain aspects, the isolated polynucleotide includes a fragment of at least 5, 10, 15, 20, 25, 30, 35, 40, 45, 50, 100, 200, 250, 500, 1000, 5000, 10,000, 25,000, 50,000, 100,000, 125,000, 250,000 or 500,000 nucleotides in length. Furthermore, in certain examples, the isolated polynucleotide includes a fragment of at least 5, 10, 15, 20, 25, 30, 35, 40, 45, 50, 100, 200, 250, 500, 1000, 5000, or 9549 contiguous nucleotides of any one of SEQ ID NOS:24493 to 64886. In another aspect, the isolated polynucleotide is at least 65, 70, 75, 80, 85, 90, 95, 96, 97, 98, 99, or 99.5% identical to the recited sequences, for example. In another aspect, the isolated nucleotide includes region that is contiguous with a region of any one of SEQ ID NOS:19473 to 21982 that includes position 300. In certain aspects, the isolated polynucleotide consists of any one of SEQ ID NOS:19473 to 21982. In other aspects, the isolated polynucleotide consists of any one of SEQ ID NOS:21983 to 24492.

The polynucleotide or an oligonucleotide of the invention can further include a detectable label. For example, the detectable label can be associated with the polynucleotide at a position corresponding to position 300 of any one of SEQ ID NOS:19473 to 21982. As discussed in more detail herein, the labeled polynucleotide can be generated, for example, during a microsequencing reaction, such as SNP-IT™ reaction.

Detectable labeling of a polynucleotide or oligonucleotide is well known in the art. Particular non-limiting examples of detectable labels include chemiluminescent labels, fluorescent labels, radiolabels, enzymes, haptens, or even unique oligonucleotide sequences.

In another embodiment, the present invention provides an isolated vector that includes a polynucleotide disclosed hereinabove. The term "vector" refers to a plasmid, virus or other vehicle known in the art that has been manipulated by insertion or incorporation of a nucleic acid sequence.

Methods that are well known in the art can be used to construct vectors, including in vitro recombinant DNA techniques, synthetic techniques, and in vivo recombination/genetic techniques (See, for example, the techniques described in Maniatis et al. 1989 Molecular Cloning A Laboratory Manual, Cold Spring Harbor Laboratory, N.Y., incorporated herein in its entirety by reference).

In another aspect, the present invention provides an isolated cell that includes the vector. The cell can be prokaryotic or eukaryotic. Techniques for incorporated vectors into prokaryotic and eukaryotic cells are well known in the art. In certain aspects, the cells are bovine cells. In other aspects, the cells are bacterial cells. In still other aspects, the cells are human cells.

In another aspect, the present invention provides a primer pair that binds to a first target region and a second target region of SEQ ID NOS:24493 to 64886, wherein the first primer of the primer pair and a second primer of the primer pair are at least 10 nucleotides in length and bind opposite strands of the target region located within 3000 nucleotides of a position corresponding to position 300 of any one of SEQ ID NOS:19473 to 21982, and prime polynucleotide synthesis from the target region in opposite directions across position 300. In another embodiment, provided herein is a primer pair that binds to a first target region and a second target region of SEQ ID NOS:19473 to 21982, wherein a first primer of the primer pair and a second primer of the primer pair are at least 10 nucleotides in length and bind opposite strands of the target region, and prime polynucleotide synthesis from the target region in opposite directions across position 300 of SEQ ID NOS:19473 to 21982. In certain aspects, the target region is within SEQ ID NOS:19473 to 21982.

In another embodiment, the present invention provides an isolated oligonucleotide that selectively binds to a target polynucleotide that includes at least 5, 10, 15, 20, 25, 30, 35, 40, 45, 50, 100, 150, 300, 500, 1000, 1500, 2000, 2500, or 3000 nucleotides, for example, of SEQ ID NOS:24493 to 64886, wherein the terminal nucleotide corresponds to position 300 of any one of SEQ ID NOS:19473 to 21982. In certain aspects, the isolated oligonucleotide includes at least 5 nucleotides of SEQ ID NO:SNP1 to SNP4000. In certain aspects, the isolated oligonucleotide is complementary to the nucleotide or a complement thereof, at position 299 or 300 of any one of SEQ ID NOS:19473 to 21982.

In another embodiment, the present invention provides an oligonucleotide that binds to any one of SEQ ID NOS:19473 to 21982, wherein the oligonucleotide is between 10 and 50 nucleotides in length, and wherein the oligonucleotide comprises at least 10 contiguous nucleotides of SEQ ID NOS: 21983 to 24492. In certain aspects, for example, the oligonucleotide is at least 15 nucleotides in length. In certain examples, the oligonucleotide binds to a region that includes position 300 of any one of SEQ ID NOS:19473 to 21982. In other examples, the oligonucleotide includes at least 15, 16, 17, 18, 19, 20, 21, 22, 23, 24 or 25 nucleotides of any one of SEQ ID NOS:21983 to 24492. The isolated oligonucleotide can be any one of SEQ ID NOS:21983 to 24492.

In another embodiment, the present invention provides an isolated oligonucleotide that includes 10 nucleotides, that selectively binds to a target polynucleotide of any one of SEQ ID NOS:19473 to 21982, wherein a terminal nucleotide of the isolated oligonucleotide binds to position 298, 299, 300, 301, or 302 of any one of SEQ ID NOS:19473 to 21982. The oligonucleotide can be, for example, 10, 15, 20, 25, 50, or 100 nucleotides in length. In certain aspects, the terminal nucleotide binds to position 300 of any one of SEQ ID NOS:19473 to 21982.

In another embodiment, the present invention provides an isolated oligonucleotide pair effective for determining a nucleotide occurrence at a single nucleotide polymorphism (SNP) corresponding to position 300 of any one of SEQ ID NOS:19473 to 21982, wherein each isolated oligonucleotide comprises at least 5 nucleotides from SEQ ID NOS:19473 to 21982 and wherein the terminal nucleotide of each oligonucleotide pair is complementary to a different nucleotide at position 300 of any one of SEQ ID NOS:19473 to 21982 or a complement thereof. In certain aspects, the specific binding pair member is a substrate for a primer extension reaction.

In another embodiment, the invention provides a method for drawing an inference regarding a trait of a bovine subject by determining the nucleotide occurrence of at least one bovine SNP that is associated with the trait. A SNP is associated with a trait when at least one nucleotide occurrence of the SNP occurs more frequently in subjects with a certain characteristic of the trait in a statistically significant manner, for example with greater than 80%, 85%, 90%, 95%, or 99% confidence. Therefore, in certain aspects, the methods include identifying whether the nucleotide occurrence is a bovine SNP allele identified herein as associated with a trait. A bovine "SNP allele" is a nucleotide occurrence of a SNP within a population of bovine animals. The inference, in certain aspects, is drawn by determining the nucleotide occurrence of one or more SNPs corresponding to position 300 of SEQ ID NOS:19473 to 21982. These SNPs are referred to herein as "associated SNPs." The inference can be drawn regarding a variety of traits as discussed herein, such as, for example, fat thickness, retail yield, marbling, tenderness, or average daily gain. In certain aspects, the bovine subject is an Angus, Charolais, Limousin, Hereford, Brahman, Simmental or Gelbvieh bovine subject.

As illustrated in the Example provided herein, a high density SNP map of the bovine genome was constructed and analyzed for the presence of SNPs that are associated with a trait at a confidence level of 0.01 or greater. The identified SNPs are referred to herein as "SNPs that are associated with a trait" or "associated SNPs." The predictive value of the associated SNPs allow a determination of the genetic potential of a bovine animal to express multiple economically important traits, termed the molecular breeding and selection value. This information is utilized to enhance the efficiency and accuracy of breeding, sorting and cloning of animals.

The analysis disclosed in the Examples herein, utilized methods of the present invention, to generate a high-density genetic map of the bovine genome based on single nucleotide polymorphic (SNP) markers. The high-density genetic map was created through a whole genome sequence of the bovine genome using the shotgun sequencing approach as described by Venter, J. C, et al., (*Science* 291:1304-1351 (2001)). Shotgun sequencing was performed with four different bovine individuals that represent different breed types. Upon whole genome assembly of the sequenced fragments all sequence variants were identified and cataloged. Sequence variants that differ by a single nucleotide became candidate SNP markers for the high-density map. The relative position of each candidate SNP within the bovine genome was determined by using the assembled human genome as scaffolding. Candidate SNPs were chosen based on their locations so that the map is evenly distributed across the bovine genome. The genetic SNP map is evenly distributed where the average genetic distance between any two adjacent markers is 0.5 cM.

Furthermore, phenotypic data from 3791 bovine animals was collected from a three by three factorial feeding and carcass data collection experiment, comparing three biological types (English, Continental and Brahman crosses) within three different days on feed (early, optimum and late). Animals were randomly assigned to treatment groups based on biological type. All cattle entered the experiment within 90 kg of body weight. These groups were blocked across starting and harvest date. Blood samples were collected on each individual animal at the start of the feeding period and assigned an electronic ID that was matched to the collection sample. At the completion of the feeding and harvest period data were compiled and analyzed for relevant statistical parameters. Statistically significant associations between specific SNPs and targeted traits were identified by methods disclosed herein for utilizing a high-density genetic SNP map in the performance of whole genome association studies in bovine animals. Using methods and results provided herein, the effect of the associated SNP on the target trait through allele frequency differences in the SNP was determined. Furthermore, as disclosed herein, SNPs that are adjacent to or in close proximity to some of the associated SNPs were identified that are associated with the same traits as an associated SNP.

As discussed in detail in the attached Examples, DNA samples were pooled from bovine subjects that represent high and low phenotypic extremes for the expression of a target trait in a population of bovine animals (e.g. high fat). The traits selected for analysis were marbling, tenderness, fat thickness, yield, and daily gain. A total of 2510 SNPs were identified that are associated with these traits (Tables 1A and 1B).

Tables 1A and 1B, both of which are filed herewith on a compact disc, disclose the SNPs identified by the analysis, and provide the SNP names for the SNPs corresponding to position 300 of SEQ ID NOS:19473 to 21982. The sequences disclosed in SEQ ID NOS:SNP1 to SNP4000 are regions from which amplicons were generated. Table 1B also indicates the location of the amplicon-generating regions within a larger bovine genomic sequence contig (SEQ ID NOS: 24493 to 64886) (See column 2 of Table 1B, labeled "In Sequence," which lists a contig name (e.g., "19866880525139") and positions (e.g. "923-1522") within the contig of an amplicon which includes the SNP at position 300. A sequence identifier for the amplicon (SEQ ID NOS: 19473-21982) is listed in Table 1A. Furthermore, Tables 1A and 1B identify the nucleotide occurrences that have been detected for each of these SNPs, and identifies traits that have been identified to be associated with these SNPs using methods disclosed herein. All of the SNPs listed in Tables 1A and 1B were associated with the respective trait(s) with a confidence level of 0.01, or higher confidence. Finally, Table 1A provides the sequence of an extension primer that was used to determine the nucleotide occurrence of the SNPs (SEQ ID NOS:21983 to 24492).

Each SNP in Tables 1A and 1B is characterized by the trait(s) found to be in association: marbling, tenderness, fat thickness, daily gain and retail yield. For each of the five traits, "High" refers to animals reaching the 90$^{th}$ percentile of that phenotypic measurement based on numeric ranking for the trait. "Low" refers to animals in the 10$^{th}$ percentile or less of that phenotypic measurement based on the numeric ranking of the trait.

In certain aspects of the invention directed at methods for inferring traits such as the traits listed in Tables 1A and 1B, nucleotide occurrences are determined for one or more associated SNPs. Therefore, in one aspect, for example, the method is used to infer fat thickness, by determining a nucleotide occurrence of at least one SNP corresponding to the SNPs indicated in Tables 1A and 1B as associated with fat thickness. For this aspect, as a non-limiting example, a nucleotide occurrence of the SNP at position 300 of SEQ ID NO:19473 can be identified and compared to the nucleotide occurrences listed in Tables 1A and 1B 1 for SEQ ID NO:19473. A thymidine residue at position 300 of SEQ ID NO:19473 infers a higher likelihood that the bovine subject will produce meat that has high tenderness. In addition, as a non-limiting example, a nucleotide occurrence at position 300 of SEQ ID NO:19474 can be determined and used alone or in combination with the nucleotide occurrence at position 300 of SEQ ID NO:19473, to infer tenderness. For example, if position 300 of both SEQ ID NO:19473 and SEQ ID NO:19474 are thymidine residues, there is an even greater likelihood that the bovine subject will produce meat that has high tenderness, than for either nucleotide occurrence alone.

In another aspect, the method is used to infer retail yield, by determining a nucleotide occurrence of at least one SNP corresponding to the SNPs indicated in Table 1A as associated with retail yield. In another aspect, the method is used to infer marbling by determining a nucleotide occurrence of at least one SNP corresponding to the SNPs indicated in Table 1A as associated with marbling. In another aspect, the method is used to infer daily gain, by determining a nucleotide occurrence of at least one SNP corresponding to the SNPs indicated in Table 1A as associated with daily gain.

For any trait, a "relatively high" characteristic, indicates greater than average, and a "relatively low" characteristic indicates less than average. For example "relatively high marbling", indicates more abundant marbling than average marbling for a bovine population. Conversely, "relatively low marbling", indicates less abundant marbling than average marbling for a bovine population. Furthermore, in certain aspects, methods of the present invention infer that a bovine subject has a significant likelihood of having a value for a trait that is within, for example, the 5th, 10th, 20th, 25th, 30th, 40th, 50th, 60th, 70th, 75th, 80th, 90th, or 95th percentile of bovine subjects for a given trait. For example, a method presented herein can provide an inference that a bovine subject has a significant likelihood of having a marbling value that is within the 10th percentile of marbling for a bovine population. SNP nucleotide occurrences listed in Tables 1A and 1B as associated with a "high" trait characteristic (e.g., high tenderness) are likely to be associated with a value greater than a 50th percentile of the bovine population for the relevant trait, and in certain aspects, in the at least 90th percentile. SNP nucleotide occurrences listed in Tables 1A and 1B as associated with a "low" trait characteristic (e.g., low tenderness) are likely to be associated with a value less than a 50th percentile of the bovine population for the relevant trait, and in certain aspects, less than or equal to the 10th percentile.

In one aspect, the methods of the invention can be utilized in combination with various hypermutable sequences, such as microsatellite nucleic acid sequences to infer traits of bovine subjects. As used herein, the term "hypermutable" refers to a nucleic acid sequence that is susceptible to instability, thus resulting in nucleic acid alterations. Such alterations include the deletion and addition of nucleotides. The hypermutable sequences of the invention are most often microsatellite DNA sequences which, by definition, are small tandem repeat DNA sequences. Thus, a combination of SNP analysis and microsatellite analysis may be used to infer a trait(s) of a bovine subject.

In another embodiment, the present invention provides a method for determining a nucleotide occurrence of a polymorphism in a bovine sample, wherein polymorphism corresponds to position 300 of any one of SEQ ID NOS:19473 to 21982. In one aspect, the nucleotide occurrence is determined by contacting a bovine polynucleotide in the sample with an oligonucleotide that binds to a target region of any one of SEQ ID NOS:24493 to 64886, wherein the target region comprises a position corresponding to position 300 of any one of SEQ ID NOS:19473 to 21982 or wherein the target region is within 3000 nucleotides of a nucleotide corresponding to position 300 of any one of SEQ ID NOS:19473 to 21982, and determining the nucleotide occurrence of a single nucleotide polymorphism (SNP) corresponding to position 300 of any one of SEQ ID NOS:19473 to 21982. The determination typically includes analyzing binding of the oligonucleotide or detecting an amplification product generated using the oligonucleotide.

In certain aspects, the target region is within 3000, 2000, 1500, 1000, 750, 500, 250, 200, 150, 100, 75, 50, 40, 30, 20 10, 9, 8, 8, 7, 6, 5, 4, 3, 2, or 1 nucleotide of a nucleotide corresponding to position 300 of any one of SEQ ID NOS: 19473 to 21982, or the target region includes position 300 of SEQ ID NOS:19473 to 21982. In certain aspects, the target region is any one of SEQ ID NOS:19473 to 21982.

In certain aspects, for example, the oligonucleotide binds to a target sequence that includes one of the SNPs and the nucleotide occurrence is determined based on the binding of the oligonucleotide to the target sequence. Methods for determining nucleotide occurrences at SNPs are disclosed herein. Some of these methods utilize flanking primer pairs. Accordingly, in one aspect, the bovine polynucleotide is contacted with a primer pair, and the nucleotide occurrence is determined using an amplification product generated using the primer pair. One or both of the primers in the primer pair can include a detectable label.

In certain examples, the terminal nucleotide of the oligonucleotide binds to the SNP position. For example, the terminal nucleotide of each oligonucleotide pair can be complementary to a different nucleotide at position 300 of any one of SEQ ID NOS:19473 to 21982 or a complement thereof. In certain aspects, one oligonucleotide is the oligonucleotide of any one of SEQ ID NOS:21983 to 24492.

In certain aspects, the method further includes managing at least one of food intake, diet composition, administration of feed additives or pharmacological treatments such as vaccines, antibiotics, hormones and other metabolic modifiers, age and weight at which diet changes or pharmacological treatments are imposed, days fed specific diets, castration, feeding methods and management, imposition of internal or external measurements and environment of the bovine subject based on the inferred trait. This management results in improved, and in some examples, a maximization of physical characteristic of a bovine subject, for example to obtain a maximum amount of high grade beef from a bovine subject, and/or to increase the chances of obtaining grade USDA Choice or Prime beef, optimize tenderness, and/or maximize retail yield from the bovine subject taking into account the inputs required to reach those endpoints.

The method can be used to discriminate among those animals where growth implants, vitamin E, and other interventions could provide the greatest value. For example, animals that do not have the traits to reach high choice or prime quality grades may be given growth implants until the end of the feeding period, thus maximizing feed efficiency while animals with a propensity to marble may not be implanted at the final stages of the feeding period to ensure maximum fat deposition intramuscularly.

The method also allows a feedlot and processor to predict the quality and yield grades of cattle in the system to optimize marketing of the fed animal or the product to meet target market specification. The method also provides information to the feedlot for purchase decisions based on the predicted economic returns from a specific supplier. Furthermore, The method allows the creation of integrated programs spanning breeders, producers, feedlots, packers and retailers.

Examples of feed additives include antibiotics, flavors and metabolic modifiers. Information from SNPs could influence use of these additives and other pharmacologic treatments depending on cattle genetic potential and stage of growth relative to expected carcass composition. Examples of feeding methods include ad-libitum versus restricted feeding, feeding in confined or non-confined conditions and number of feedings per day. Information from SNPs relative to cattle health, immune status or stress response could be used to influence choice of optimum feeding methods for individual cattle.

In another embodiment, methods are provided for selecting a given animal for shipment at the optimum time, considering the animal's condition, performance and market factors, the ability to grow the animal to its optimum individual potential of physical and economic performance, and the ability to record and preserve each animal's performance history in the feedlot and carcass data from the packing plant for use in cultivating and managing current and future animals for meat production. These methods allow management of the current diversity of cattle to improve the beef product quality and uniformity, thus improving revenue generated from beef sales.

The methods can use a bioeconomic valuation method that establishes the economic value of a bovine subject, or a group of bovine subjects, such as those in a pen, to optimize profits from beef production. Accordingly, in another embodiment, the present invention provides a method for establishing the economic value of a bovine subject. According to the method, an inference is drawn regarding a trait of the bovine subject from a nucleic acid sample of the bovine subject. The inference is drawn by a method that includes identifying nucleotide occurrences for at least one single nucleotide polymorphism (SNP), wherein the nucleotide occurrence is associated with the trait, and wherein the trait affects the value of the bovine subject. Furthermore, the inference, in certain aspects, is drawn by determining the nucleotide occurrence of at least one SNP corresponding to position 300 of SEQ ID NOS:19473 to 21982.

The method, in certain examples, includes identification of the causative mutation influencing the trait directly or the determination of 1 or more SNPs that are in linkage disequilibrium with the associated trait.

The method can include a determination of the nucleotide occurrence of at least 2 SNPs. At least 2 SNPs can form all or a portion of a haplotype, wherein the method identifies a haplotype allele that is in linkage disequilibrium and thus associated with the trait. Furthermore, the method can include identifying a diploid pair of haplotype alleles.

A method according to this aspect of the invention can further include using traditional factors affecting the economic value of the bovine subject in combination with the inference based on nucleotide occurrence data to determine the economic value of the bovine subject.

As used herein, the term "at least one", when used in reference to a gene, SNP, haplotype, or the like, means 1, 2, 3, 4, 5, 6, 7, 8, 9, 10, etc., up to and including all of the haplotype alleles, genes, and/or SNPs of the bovine genome. Reference to "at least a second" gene, SNP, or the like, means two or more, i.e., 2, 3, 4, 5, 6, 7, 8, 9, 10, etc., bovine genes, SNPs, or the like.

Polymorphisms are allelic variants that occur in a population that can be a single nucleotide difference present at a locus, or can be an insertion or deletion of one, a few or many consecutive nucleotides. As such, a single nucleotide polymorphism (SNP) is characterized by the presence in a population of one or two, three or four nucleotides (i.e., adenosine, cytosine, guanosine or thymidine), typically less than all four nucleotides, at a particular locus in a genome such as the human genome. It will be recognized that, while the methods of the invention are exemplified primarily by the detection of SNPs, the disclosed methods or others known in the art similarly can be used to identify other types of bovine polymorphisms, which typically involve more than one nucleotide.

The term "haplotypes" as used herein refers to groupings of two or more SNPs that are physically present on the same chromosome which tend to be inherited together except when recombination occurs. The haplotype provides information regarding an allele of the gene, regulatory regions or other genetic sequences affecting a trait The linkage disequilibrium and, thus, association of a SNP or a haplotype allele(s) and a bovine trait can be strong enough to be detected using simple genetic approaches, or can require more sophisticated statistical approaches to be identified.

Numerous methods for identifying haplotype alleles in nucleic acid samples are known in the art. In general, nucleic acid occurrences for the individual SNPs are determined and then combined to identify haplotype alleles. There are several algorithms for haplotype reconstruction based on pedigree analysis. These are the Maximum Likelihood method ((Excofier, L., and Slatkin, M., *Mol. Biol. Evol.* 12: 921-927 (1995)), the parsimony method created by Clark, A. G., *Mol. Biol. Evol.* 7: 111-122 (1990) and the phase reconstruction method of Stephens, M., et al., *Am. J. Hum. Genet.* 68:978-989, 2001, which is incorporated herein by reference) can be applied to the data generated regarding individual nucleotide occurrences in SNP markers of the subject, in order to determine alleles for each haplotype in a subject's genotype. Alternatively, haplotypes can also be determined directly, for each pair of sites, by allele-specific PCR (Clark, A. G. et al., *Am. J. Hum. Genet.* 63: 595-612 (1998).

As used herein, the term "infer" or "inferring", when used in reference to a trait, means drawing a conclusion about a trait using a process of analyzing individually or in combination, nucleotide occurrence(s) of one or more SNP(s), which can be part of one or more haplotypes, in a nucleic acid sample of the subject, and comparing the individual or combination of nucleotide occurrence(s) of the SNP(s) to known relationships of nucleotide occurrence(s) of the SNP(s) and the trait. As disclosed herein, the nucleotide occurrence(s) can be identified directly by examining nucleic acid molecules, or indirectly by examining a polypeptide encoded by a particular gene where the polymorphism is associated with an amino acid change in the encoded polypeptide.

Relationships between nucleotide occurrences of one or more SNPs or haplotypes and a trait can be identified using known statistical methods. A statistical analysis result which shows an association of one or more SNPs or haplotypes with a trait with at least 80%, 85%, 90%, 95%, or 99%, or 95% confidence, or alternatively a probability of insignificance less than 0.05, can be used to identify SNPs and haplotypes. These statistical tools may test for significance related to a null hypothesis that an on-test SNP allele or haplotype allele is not significantly different between groups with different traits. If the significance of this difference is low, it suggests the allele is not related to a trait.

As another example, associations between nucleotide occurrences of one or more SNPs or haplotypes and a trait (i.e. selection of significant markers) can be identified using a two part analysis in the first part, DNA from animals at the extremes of a trait are pooled, and the allele frequency of one or more SNPs or haplotypes for each tail of the distribution is estimated. Alleles of SNPs and/or haplotypes that are apparently associated with extremes of a trait are identified and are used to construct a candidate SNP and/or haplotype set. Statistical cut-offs are set relatively low to assure that significant SNPs and/or haplotypes are not overlooked during the first part of the method.

During the second stage, individual animals are genotyped for the candidate SNP and/or haplotype set. The second stage is set up to account for as much of the genetic variation as possible in a specific trait without introducing substantial error. This is a balancing act of the prediction process. Some animals are predicted with high accuracy and others with low accuracy.

In diploid organisms such as bovines, somatic cells, which are diploid, include two alleles for each single-locus haplotype. As such, in some cases, the two alleles of a haplotype are referred to herein as a genotype or as a diploid pair, and the analysis of somatic cells, typically identifies the alleles for each copy of the haplotype. Methods of the present invention can include identifying a diploid pair of haplotype alleles. These alleles can be identical (homozygous) or can be different (heterozygous). Haplotypes that extend over multiple loci on the same chromosome include up to 2 to the Nth power alleles where N is the number of loci. It is beneficial to express polymorphisms in terms of multi-locus (i.e. multi SNP) haplotypes because haplotypes offer enhanced statistical power for genetic association studies. Multi-locus haplotypes can be precisely determined from diploid pairs when the diploid pairs include 0 or 1 heterozygous pairs, and N or N−1 homozygous pairs. When multi-locus haplotypes cannot be precisely determined, they can sometimes be inferred by statistical methods. Methods of the invention can include identifying multi-locus haplotypes, either precisely determined, or inferred.

A sample useful for practicing a method of the invention can be any biological sample of a subject, typically a bovine subject, that contains nucleic acid molecules, including portions of the gene sequences to be examined, or corresponding encoded polypeptides, depending on the particular method. As such, the sample can be a cell, tissue or organ sample, or can be a sample of a biological material such as a body fluid, for example blood, milk, semen, saliva, or can be hair, tissue, and the like. A nucleic acid sample useful for practicing a method of the invention can be deoxyribonucleic (DNA) acid or ribonucleic acids (RNA). The nucleic acid sample generally is a deoxyribonucleic acid sample, particularly genomic DNA or an amplification product thereof. However, where heteronuclear ribonucleic acid which includes unspliced mRNA precursor RNA molecules and non-coding regulatory molecules such as RNA is available, a cDNA or amplification product thereof can be used.

Where each of the SNPs of the haplotype is present in a coding region of a gene(s), the nucleic acid sample can be DNA or RNA, or products derived therefrom, for example, amplification products. Furthermore, while the methods of the invention generally are exemplified with respect to a nucleic acid sample, it will be recognized that particular haplotype alleles can be in coding regions of a gene and can result in polypeptides containing different amino acids at the positions corresponding to the SNPs due to non-degenerate codon changes. As such, in another aspect, the methods of the invention can be practiced using a sample containing polypeptides of the subject.

In one embodiment, DNA samples are collected and stored in a retrievable barcode system, either automated or manual, that ties to a database. Collection practices include systems for collecting tissue, hair, mouth cells or blood samples from individual animals at the same time that ear tags, electronic identification or other devices are attached or implanted into the animal. Tissue collection devices can be integrated into the tool used for placing the ear tag. Body fluid samples are collected and can be stored on a membrane bound system. All methods could be automatically uploaded into a primary database.

The sample is then analyzed on the premises or sent to a laboratory where a high-throughput genotyping system is used to analyze the sample. Traits are predicted in the field, in real-time, or in the laboratory and forwarded electronically to a feedlot. The feedlot then uses this information to sort and manage animals to maximize profitability and marketing potential.

The present invention can also be used to provide information to breeders to make breeding, mating, and or cloning decisions. This invention can also be combined with traditional genetic evaluation methods to improve selection, mating, or cloning strategies.

The subject of the present invention can be any bovine subject, for example a bull, a cow, a calf, a steer, or a heifer or any bovine embryo or tissue, and includes all breeds of bovines. For methods of the invention directed at sorting bovine subjects, managing bovine subjects, improving profits related to selling beef from a bovine subject, the animal can be a young bovine subject ranging in ages from conception to the time the animal is harvested and beef and other commercial products obtained. The method of the present invention can be performed after the animal is purchased and first enters the feedlot.

A "trait" is a characteristic of an organism that manifests itself in a phenotype. Many traits are the result of the expression of a single gene, but some are polygenic (i.e., result from simultaneous expression of more than one gene). A "phenotype" is an outward appearance or other visible characteristic of an organism. Many different non-bovine livestock traits can be inferred by methods of the present invention. Traits analyzed in methods of the present invention include, but are not limited to, marbling, tenderness, quality grade, quality yield, muscle content, fat thickness, feed efficiency, red meat yield, average daily weight gain, disease resistance, disease susceptibility, feed intake, protein content, bone content, maintenance energy requirement, mature size, amino acid profile, fatty acid profile, milk production, hide quality, susceptibility to the buller syndrome, stress susceptibility and response, temperament, digestive capacity, production of calpain, calpastatin and myostatin, pattern of fat deposition, ribeye area, fertility, ovulation rate, conception rate, fertility, heat tolerance, environmental adaptability, robustness, susceptibility to infection with and shedding of pathogens such as *E. Coli, Salmonella* sp. and other human pathogens.

Methods of the present invention can be used to infer more than one trait. For example a method of the present invention can be used to infer a population of traits. Accordingly, a method of the present invention can infer, for example, quality grade, muscle content, and feed efficiency. This inference can be made using one SNP or a population or series of SNPs. Thus, a single SNP can be used to infer multiple traits; multiple SNPs can be used to infer multiple traits; or a single SNP can be used to infer a single trait. Where certain traits have either positive or negative correlations to each other, the methods allow identification of all SNPs that enhance or uncouple the correlation.

In another aspect, the present invention provides a method for improving profits related to selling beef from a bovine subject. The method includes drawing an inference regarding a trait of the bovine subject from a nucleic acid sample of the bovine subject. The method is typically performed by a method that includes identifying a nucleotide occurrence for at least one single nucleotide polymorphism (SNP), wherein the nucleotide occurrence is associated with the trait, and wherein the trait affects the value of the animal or its products. Furthermore, the method includes managing at least one of food intake, diet composition, administration of feed additives or pharmacological treatments such as vaccines, antibiotics, hormones and other metabolic modifiers, age and weight at which diet changes or pharmacological treatments are imposed, days fed specific diets, castration, feeding methods and management, imposition of internal or external measurements and environment of the bovine subject based on the inferred trait. Then at least one bovine commercial product, typically meat or milk, is obtained from the bovine subject.

Methods according to this aspect of the present invention can utilize a bioeconomic model, such as a model that estimates the net value of one or more bovine subjects based on one or more traits. By this method, traits of one, or a series of traits are inferred, for example, an inference regarding several characteristics of beef that will be obtained from the bovine subject. This inference is typically made before the bovine subjects enter the feedlot. The inferred trait information then can be entered into a model that uses the information to estimate a value for the bovine subject, or beef from the bovine subject, based on the traits. The model is typically a computer model. Values for the bovine subjects can be used to segregate the animals. Furthermore, various parameters that can be controlled during maintenance and growth of the bovine subjects can be input into the model in order to affect the way the animals are raised in order to obtain maximum value for the bovine subject when it is harvested.

In certain embodiments, meat or milk can be obtained at a time point that is affected by the inferred trait and one or more of the food intake, diet composition, and management of the bovine subject. For example, where the inferred trait of a bovine subject is high feed efficiency, which can be identified in quantitative or qualitative terms, meat or milk can be obtained at a time point that is sooner than a time point for a bovine subject with low feed efficiency. As another example, bovine subjects with different feed efficiencies can be separated, and those with lower feed efficiencies can be implanted with growth promotants or fed metabolic partitioning agents in order to maximize the profitability of a single bovine subject.

In another aspect, the present invention provides methods that allow effective measurement and sorting of animals individually, accurate and complete record keeping of genotypes and traits or characteristics for each animal, and production of an economic end point determination for each animal using growth performance data. Accordingly, the present invention provides a method for sorting bovine subjects. The method includes inferring a trait for both a first bovine subject and a second bovine subject from a nucleic acid sample of the first bovine subject and the second bovine subject. The inference is made by a method that includes identifying the nucleotide occurrence of at least one single nucleotide polymorphism (SNP), wherein the nucleotide occurrence is associated with the trait. The method further includes sorting the first bovine subject and the second bovine subject based on the inferred trait.

The method can further include measuring a physical characteristic of the first bovine subject and the second bovine subject, and sorting the first bovine subject and the second bovine subject based on both the inferred trait and the measured physical characteristic. The physical characteristic can be, for example, weight, breed, type or frame size, and can be measured using many methods known in the art, such as by using ultrasound.

In another aspect, the present invention provides methods that use analysis of bovine genetic variation to improve the genetics of the cattle population to produce animals with consistent desirable characteristics, such as animals that yield a high percentage of lean meat and a low percentage of fat efficiently. Accordingly, in one aspect the present invention provides a method for selection and breeding of bovine subjects for a trait. The method includes inferring the genetic potential for a trait or a series of traits in a group of bovine candidates for use in breeding programs from a nucleic acid sample of the bovine candidates. The inference is made by a method that includes identifying the nucleotide occurrence of at least one single nucleotide polymorphism (SNP), wherein the nucleotide occurrence is associated with the trait or traits. Individuals are then selected from the group of candidates with a desired performance for the trait or traits for use in breeding programs. Progeny resulting from mating of selected parents would contain the optimum combination of traits, thus creating an enduring genetic pattern and line of animals with specific traits. These lines could be monitored for purity using the original SNP markers and could be identified from the entire population of bovines and protected from genetic theft.

In another aspect the present invention provides a method for cloning a bovine subject with a specific trait or series of traits. The method includes identifying nucleotide occurrences of at least one or at least two SNPs for the bovine subject, isolating a progenitor cell from the bovine subject, and generating a cloned bovine from the progenitor cell. The method can further include before identifying the nucleotide occurrences, identifying the trait of the bovine subject, wherein the bovine subject has a desired trait and wherein the at least one or at least two SNPs affect the trait.

Methods of cloning cattle are known in the art and can be used for the present invention. (See e.g., Bondioli, "Commercial cloning of cattle by nuclear transfer", In: Symposium on Cloning Mammals by Nuclear Transplantation, Seidel (ed), pp. 35-38, (1994); Willadsen, "Cloning of sheep and cow embryos," *Genome,* 31:956, (1989); Wilson et al., "Comparison of birth weight and growth characteristics of bovine calves produced by nuclear transfer (cloning), embryo transfer and natural mating", *Animal Reprod. Sci.,* 38:73-83, (1995); and Barnes et al., "Embryo cloning in cattle: The use of in vitro matured oocytes", *J. Reprod. Fert.,* 97:317-323, (1993)). These methods include somatic cell cloning (See e.g., Enright B. P. et al., "Reproductive characteristics of cloned heifers derived from adult somatic cells," *Biol. Reprod.,* 66:291-6 (2002); Bruggerhoff K., et al., "Bovine somatic cell nuclear transfer using recipient oocytes recovered by ovum pick-up: effect of maternal lineage of oocyte donors," *Biol. Reprod.,* 66:367-73 (2002); Wilmut, I., et al., "Somatic cell nuclear transfer," *Nature,* 419:583 (2002); Galli, C., et al., "Bovine embryo technologies," *Theriogenology,* 59:599 (2003); Heyman, Y., et al., "Novel approaches and hurdles to somatic cloning in cattle," *Cloning Stem Cells,* 4:47 (2002)).

Furthermore, methods have been reported for culturing bovine embryonic stem cells (See e.g., Saito, et al., "Bovine embryonic stem cell-like cell lines cultured over several passages," *Roux's Arch. Dev. Biol.,* 201:i34-i40, 1992). These cells can be used to produce tissues with predetermined characteristics based on SNP information using the methods of the present invention.

This invention identifies animals that have superior traits, predicted very accurately, that can be used to identify parents of the next generation through selection. These methods can be imposed at the nucleus or elite breeding level where the improved traits would, through time, flow to the entire population of animals, or could be implemented at the multiplier or foundation parent level to sort parents into most genetically desirable. This invention provides a method for determining the optimum male and female parent to maximize the genetic components of dominance and epistasis thus maximizing heterosis and hybrid vigor in the market animals.

In another aspect, the present invention provides a bovine subject resulting from the selection and breeding aspect or the cloning aspect of the invention, discussed above.

In another aspect, the present invention provides a method of tracking meat of a bovine subject. The method includes identifying nucleotide occurrences for a series of genetic markers of the bovine subject, identifying the nucleotide occurrences for the series of genetic markers for a meat sample, and determining whether the nucleotide occurrences of the bovine subject are the same as the nucleotide occurrences of the meat sample. In this method identical nucleotide occurrences indicate that the meat sample is from the bovine subject. The tracking method provides, for example, a method for historical and epidemiological tracking the location of an animal from embryo to birth through its growth period, to the feedlot and harvest and finally the retail product after the it has reached the consumer.

The series of genetic markers can be a series of single nucleotide polymorphisms (SNPs). The method can further include comparing the results of the above determination with a determination of whether the meat is from the bovine subject made using another tracking method. In this embodiment, the present invention provides quality control information that improves the accuracy of tracking the source of meat by a single method alone.

The nucleotide occurrence data for the bovine subject can be stored in a computer readable form, such as a database. Therefore, in one example, an initial nucleotide occurrence determination can be made for the series of genetic markers for a young bovine subject and stored in a database along with information identifying the bovine subject. Then, after meat from the bovine subject is obtained, possibly months or years after the initial nucleotide occurrence determination, and before and/or after the meat is shipped to a customer such as, for example, a wholesale distributor, a sample can be obtained from the meat and nucleotide occurrence information determined using methods discussed herein. The database can then be queried using a user interface as discussed herein, with the nucleotide occurrence data from the meat sample to identify the bovine subject.

A series of markers or a series of SNPs as used herein, can include a series of at least 2, 3, 4, 5, 6, 7, 8, 9, 10, 15, 20, 25, 30, 35, 40, 45, 50, 75, 100, 150, 200, 250, 500, 1000, 2000, 2500, 5000, or 6000 markers, for example.

In another aspect, the present invention provides a method for diagnosing a health condition of a bovine subject. The method includes drawing an inference regarding a trait of the bovine subject for the health condition, from a nucleic acid sample of the subject. The inference is drawn by identifying, in the nucleic acid sample, at least one nucleotide occurrence of a single nucleotide polymorphism (SNP), wherein the nucleotide occurrence is associated with the trait.

The nucleotide occurrence of at least 2 SNPs can be determined. The at least 2 SNPs can form a haploytpe, wherein the method identifies a haplotype allele that is associated with the trait. The method can include identifying a diploid pair of haplotype alleles for one or more haplotypes.

The health condition for this aspect of the invention, is resistance to disease or infection, susceptibility to infection with and shedding of pathogens such as *E. Coli, salmonella, listeria*, prion diseases, and other organisms potentially pathogenic to humans, regulation of immune status and response to antigens, susceptibility to bloat, liver abscess or the buller syndrome, previous exposure to infection or parasites, or health of respiratory and digestive tissues.

The present invention in another aspect provides a method for inferring a trait of a bovine subject from a nucleic acid sample of the subject, that includes identifying, in the nucleic acid sample, at least one nucleotide occurrence of a single nucleotide polymorphism (SNP). The nucleotide occurrence is associated with the trait, thereby allowing an inference of the trait.

These embodiments of the invention are based, in part, on a determination that single nucleotide polymorphisms (SNPs), including haploid or diploid SNPs, and haplotype alleles, including haploid or diploid haplotype alleles, allow an inference to be drawn as to the trait of a subject, particularly a bovine subject.

Accordingly, methods of the invention can involve determining the nucleotide occurrence of at least 2, 3, 4, 5, 10, 20, 30, 40, 50, etc. SNPs. The SNPs can form all or part of a haploytpe, wherein the method can identify a haplotype allele that is associated with the trait. Furthermore, the method can include identifying a diploid pair of haplotype alleles.

In another embodiment, the present invention provides a method for identifying a bovine genetic marker that influences at least one trait by analyzing bovine genetic markers of a genome-wide genetic marker map for association with the trait. The genetic marker can be a single nucleotide polymorphism (SNP), or can be at least two SNPs that influence the trait. Because the method can identify at least two SNPs, and in some embodiments, many SNPs, the method can identify not only additive genetic components, but non-additive genetic components such as dominance (i.e. dominating trait of an allele of one gene over an allele of a another gene) and epistasis (i.e. interaction between genes at different loci). Furthermore, the method can uncover pleiotropic effects of SNP alleles (i.e. SNP alleles or haplotypes effects on many different traits), because many traits can be analyzed for their association with many SNPs using methods disclosed herein.

In one aspect, expression products of genes near the at least two identified genetic markers are analyzed, to determine whether the expression products interact. In certain aspects, at least 2 SNPs are identified for inferring the genetic potential of a bovine animal for one, two, or more traits. At least 2 of the single nucleotide polymorphisms are located on different chromosomes. Furthermore, at least 2 of the single nucleotide polymorphisms can be separated by at least 10,000 base pairs on the bovine genome. In certain examples, at least 2 of the single nucleotide polymorphisms occur in different genes.

Accordingly, the present invention provides methods for identifying genes, chromosomal regions and SNP markers in bovine animals that account for a large proportion of the additive and non-additive genetic variation observed for any trait that has a genetic component. The methods and systems of the present invention utilize information regarding genetic diversity among cattle, particularly single nucleotide polymorphisms (SNPs), and the effect of nucleotide occurrences of SNPs on economically important traits.

The present invention provides methods to allow the simultaneous discovery of any and all SNP markers that associate with one or more traits in one or more regions throughout the entire genome. Furthermore, the present invention provides methods for utilization of the predictive diagnostic to determine the genetic potential of an animal to express any targeted trait(s). The genetic potential of a bovine animal to express multiple economically important traits, termed the molecular breeding and selection value, is utilized to enhance the efficiency and accuracy of breeding, sorting and cloning of animals.

The present invention provides methods for developing a high-density genetic map of the bovine genome based on single nucleotide polymorphic (SNP) markers. The high-density genetic map is created through a whole genome sequence of the bovine genome using the shotgun sequencing approach. Shotgun sequencing is performed with several different bovine individuals that represent different breed types. Upon whole genome assembly of the sequenced fragments all sequence variants are identified and cataloged. Sequence variants that differ by a single nucleotide become candidate SNP markers for the high-density map. The relative position of each candidate SNP within the bovine genome is determined by using the assembled human genome as scaffolding. Candidate SNPs are chosen based on their locations so that the map is evenly distributed across the bovine genome. The invention includes methods for creating an evenly distributed genetic SNP map where the average genetic distance between any two adjacent markers is 0.5 cM (i.e. 500,000 nucleotides).

Furthermore, in one embodiment, the present invention provides methods for utilizing a high-density genetic SNP map in the performance of whole genome association studies in bovine animals and the identification of statistically significant associations between specific SNPs and targeted traits. The invention provides methods for inferring the effect of the associated SNP on the target trait through allele frequency differences in the SNP. Furthermore, the invention provides methods for identifying all SNPs that are adjacent to or in close proximity to the associated SNP and ascertaining the effect these SNPs have on the target trait, as disclosed in more detail hereinbelow.

The invention provides methods for pooling DNA samples from bovine individuals that represent high and low phenotypic extremes for the expression of a target trait in a population of bovine animals. The target trait can be any trait that has a genetic component and where phenotypic differences for the trait can be measured in bovine animals, for example marbling, tenderness, fat thickness, yield, daily gain, or meat quality grade.

The invention provides methods for identifying all genomic regions, and any SNP or set of SNPs contained in these regions, that effect the expression of a target trait. For example, an inference can be drawn regarding a beef characteristic such as marbling or red meat yield and allele frequency differences in one or more SNPs.

The methods infer the discovery of one or more, and in some cases, all SNPs that show association to a target trait and therefore, account for a large proportion of the genetic variation observed in the expression of the trait in a population of bovine animals. The methods allow identification of SNPs that account for additive as well as non-additive genetic variation, such as dominance and epistasis, observed in the expression of the trait.

The methods infer the discovery of any and all SNPs that show association to one or more target traits. Furthermore, whereby certain traits have either positive or negative correlations to each other, the methods allow identification of all SNPs that enhance or uncouple the correlation. For example, the presence of external fat on beef carcasses is highly correlated with marbling or intramuscular fat. External fat is an undesirable trait that causes discounts in beef carcasses, whereas marbling is a desirable trait that results in premiums. The present invention provides methods for the identification of all SNPs that may uncouple the correlation between external fat and marbling, for example.

In another aspect, the present invention provides a method for developing a predictive diagnostic through the identification of one or more, and in certain aspects all SNPs that are associated with multiple traits having economic significance in bovines, and any and all SNPs that affect any single trait that are located throughout the entire bovine genome. The methods of the invention result in the development of a predictive diagnostic system for determining the genetic potential of individual animals for any trait that has a genetic component.

In another aspect, the present invention provides a method for utilizing a predictive diagnostic to determine the genetic potential of a bovine animal for multiple traits located across multiple genomic regions. The genetic potential determination for the expression of multiple traits in a bovine animal is referred to as the molecular breeding and selection value. The present invention provides methods for using the molecular breeding and selection value to enhance efficiencies and accuracy of breeding, sorting, purchasing and cloning of individual animals.

Accordingly, nucleotide occurrences can be determined for essentially all, or all of the SNPs of a high-density, whole genome SNP map. This approach has the advantage over traditional approaches in that since it encompasses the whole genome, it identifies potential interactions of gene products expressed from genes located anywhere on the genome without requiring preexisting knowledge regarding a possible interaction between the gene products. An example of a high-density, whole genome SNP map is a map of at least about 1 SNP per 10,000 kb, at least 1 SNP per 500 kb or about 10 SNPs per 500 kb, or at least about 25 SNPs or more per 500 kb. Definitions of densities of markers may change across the genome and are determined by the degree of linkage disequilibrium from marker to marker.

In another embodiment of the invention, a method is provided for identifying SNPs that are associated with a trait by using the associated SNPs disclosed herein. The method is based on the fact that other markers in close proximity to the associated SNP marker will also associate with the trait because markers in linkage disequilibrium with the associated SNP marker will also be in linkage disequilibrium with the gene(s) influencing the trait. SNPs in linkage disequilibrium can be used in lieu of determining a SNP or mutation to predict the presence or absence of a phenotypic trait or contributor to a phenotypic trait. Accordingly, in certain embodiments, the present invention provides a method for identifying a SNP associated with a trait, that includes identifying a test SNP that is in disequilibrium with a SNP corresponding to position 300 of SEQ ID NOS:19473 to 21982.

As illustrated in the Examples section, it has been determined that disequilibrium exists across the region of 500,000 bp from the associated SNP in each direction. Other markers within this 500,000 bp region will also be in disequilibrium with the associated SNP and with the trait of interest, and can be used to infer associations with the trait of interest. Genomic segments containing the markers can be adjacent to the associated SNP marker or contained within a separate island of sequence distant from the associated SNP.

Genetic markers within 500,000 bp of the associated SNPs disclosed herein in Tables 1A and 1B (position 300 of SEQ ID NOS:19473 to 21982), can be discovered by a number of different methods known in the art. In one aspect of the invention, bovine sequence that is within 500,000 bp of the associated SNP can be used to identify new DNA markers. This sequence can be created from whole-genome shotgun sequencing, BAC-sequencing, or sequence generated from comparative maps. The bovine sequence can be used to develop bovine specific sequencing primers. These primers can be used to sequence at least 2 individual bovine animals and the alignments from these sequences can be used to identify SNP markers and microsatellite markers.

New markers can also be discovered using heterologous sequences from other mammalian species. Degenerative primers are developed from regions of known homology among species and used in PCR. Amplification products are sequenced and used to develop bovine specific primers.

These new markers can be genotyped in pools of animals or individual animals representing the high and low ends of the phenotypic distribution for the trait to determine association between the new marker(s) and the trait. Markers with a significantly different allele frequency in the high and low groups are also in disequilibrium with the trait.

Accordingly, in another embodiment, the present invention provides a method for identifying a bovine single nucleotide polymorphism (SNP) associated with a trait that includes identifying a test SNP in a target region of a bovine genome, wherein the target region is less than or equal to about 500,000 nucleotides from a SNP position corresponding to position 300 of one of SEQ ID NOS:19473 to 21982, and identifying an association of the test SNP to the trait. In certain aspects, the target region consists of at least 20 contiguous nucleotides of SEQ ID NOS:24493 to 64886. In other aspects, the target region consists of at least 20 contiguous nucleotides of SEQ ID NOS:19473 to 21982.

In certain aspects, the test SNP is located less than or equal to about 500,000, 400,000, 300,000, 250,000, 200,000, 100,000, 50,000, 25,000, 10,000, 5,000, 1,000, or 100 nucleotides from a position corresponding to position 300 of at least one of SEQ ID NOS:19473 to 21982. The test SNP is expected to be associated with the same trait as a SNP that corresponds to position 300 of SEQ ID NOS:19473 to 21982 that is located less than or equal to about 500,000 nucleotides from the test SNP, as discussed further herein.

The trait can be any bovine trait as discussed herein. For example, the trait can be marbling, tenderness, quality grade, muscle content, fat thickness, feed efficiency, red meat yield, average daily weight gain, disease resistance, disease susceptibility, feed intake, protein content, bone content, maintenance energy requirement, mature size, amino acid profile, fatty acid profile, milk production, susceptibility to the buller syndrome, stress susceptibility and response, temperament, digestive capacity, production of calpain, caplastatin and myostatin, pattern of fat deposition, ribeye area, fertility, ovulation rate, conception rate, fertility, susceptibility to infection with or shedding of pathogens. In certain specific examples, the trait is fat thickness, retail yield, tenderness, marbling, or average daily gain.

In another embodiment, the present invention provides a method for identifying a bovine gene associated with a trait, by identifying an open reading frame present in a target region of the bovine genome, wherein the target region is located on the bovine genome less than or equal to about 500,000 nucleotides of a single nucleotide polymorphism (SNP) corresponding to position 300 of any one of SEQ ID NOS:19473 to 21982, and analyzing the open reading frame to determine whether it affects the trait.

In certain aspects, the target region is located less than or equal to about 500,000, 400,000, 300,000, 250,000, 200,000, 100,000, 50,000, 25,000, 10,000, 5,000, 1,000, 100, or 50 nucleotides from a single nucleotide polymorphism (SNP) corresponding to position 300 of any one of SEQ ID NOS: 19473 to 21982.

It will be recognized that a variety of methods can be used to determine whether the open reading frame affects a trait. For example, biochemical methods can be performed to determine a biochemical function for the product of the open gene product. The biochemical function can be compared to known biochemical functions related to the trait. Furthermore, the open reading frame can be mutated and the affects of the mutations on a target trait can be analyzed.

In another embodiment the present invention provides a method for identifying a target bovine polynucleotide affecting a trait, that includes providing a polynucleotide derived from a bovine subject, or sequence information thereof; and determining whether the polynucleotide is at least 90% identical to a SNP-containing polynucleotide. The determination can be carried out by comparing the polynucleotide or the sequence information to a polynucleotide consisting essentially of:

a) a polynucleotide according to any one of SEQ ID NOS: 19473 to 21982;

b) a contiguous fragment of a polynucleotide according to any one of SEQ ID NOS:24493 to 64886 that is at least 300 nucleotides in length and that comprises a single nucleotide polymorphism corresponding to position 300 of one of SEQ ID NOS:19473 to 21982, wherein the polymorphism is associated with the trait; or c) a complement of a) or b).

If a polynucleotide is identified as at least 90% identical to the SNP-containing polynucleotide, the bovine polynucleotide is a target polynucleotide for the trait.

In certain aspects, the polynucleotide is derived from a bovine subject that includes bovine genomic sequences. In another aspect, the present invention provides an isolated polynucleotide identified according to this method.

The invention, in another aspect includes methods for creating a high density bovine SNP map. The SNP markers and their surrounding sequence are compared to model organisms, for example human and mouse genomes, where the complete genomic sequence is known and syntenic regions identified. The model organism map may serve as a template for ensuring complete coverage of the animal genome. The finished map has markers spaced in such a way to maximize the amount of linkage disequilibrium in a specific genetic region.

This map is used to mark all regions of the chromosomes, in a single experiment, utilizing thousands of experimental animals in an association study, to correlate genomic regions with complex and simple traits. These associations can be further analyzed to unravel complex interactions among genomic regions that contribute to the targeted trait or other traits, epistatic genetic interactions and pleiotropy. The invention of regional high density maps can also be used to identify targeted regions of chromosomes that influence traits.

Accordingly, in embodiments where SNPs that affect the same trait are identified that are located in different genes, the method can further include analyzing expression products of genes near the identified SNPs, to determine whether the expression products interact. As such, the present invention provides methods to detect epistatic genetic interactions. Laboratory methods are well known in the art for determining whether gene products interact.

The method can be useful for inferring a beef characteristic from a nucleic acid sample of the subject animal (i.e., the trait is a characteristic of beef). Beef characteristics that can be inferred by methods of the present invention include, for example, overall quality, marbling, red meat yield, tenderness, and the like. Accordingly, the present invention provides methods for identifying live cattle that have or that lack the genetic potential to produce beef that is well-marbled. Such information could be used by the cattle producer to channel calves into particular feeding regimens and to meet the requirements of specific marketing programs. Such information could also be used to identify cattle that are genetically superior candidates for breeding and/or cloning. Such information could also be used to identify cattle that are genetically inferior candidates to be screened out of a breeding or cloning program.

Where the trait is overall quality, the method can infer an overall average USDA quality grade for beef obtained from the non-bovine livestock subject. For example, the quality grades can include one of the current eight USDA quality grades (i.e., from highest to lowest, prime, choice, select, standard, commercial, utility, cutter and canner). Alternatively, the method can infer the best or the worst quality grade expected for beef obtained from the non-bovine livestock subject. Additionally, as indicated above, the trait can be a characteristic used to classify beef, such as color, texture, firmness, and marbling, a term which is used to describe the relative amount and distribution of intramuscular fat of the beef. Well-marbled and well-distributed beef from steers and heifers, i.e., beef that contains substantial amounts of intramuscular fat relative to muscle, is classified as prime or choice; whereas, beef that is not marbled is classified as select. Beef that is classified as prime or choice, typically, is sold at higher prices than beef that is classified into lower quality grades.

Where the trait is red meat yield, the method can predict the total and percentage of edible product from a harvested animal. For example, Yield grade is assigned to an animal from an estimate of its back fat thickness, kidney-pelvic-heart fat, ribeye area and carcass weight. Grades range from 1 to 5, with 1 being the greatest retail product yield assignment. This method can predict the traits for red meat yield and quality grade and tailor a feeding, management and harvesting program to optimize the value of the animal.

The methods of the present invention that infer a trait can be used in place of present methods used to determine the trait, or can be used to further substantiate a classification of beef using present methods (e.g., visual inspection of a region between the 12th and 13th rib of a beef carcass by a certified USDA grader). Where the trait is tenderness, for example, methods of the present invention can infer from a sample of a bovine subject, such as a live bovine subject, whether beef, if cooked properly, would be tender. The method can be used in place of current post-mortem taste tests or shear force methods, or can be used to improve the accuracy of determinations made by these traditional methods.

In aspects of the present invention directed at identifying a bovine genetic marker that influences a trait, present methods for determining a trait, such as a characteristic of beef, can be used in the methods to identify an association between a genetic marker, typically at least one SNP or haplotype, with a trait. For example, DNA samples from bovine subjects can be obtained, and nucleotide occurrences for at least one SNP in the DNA samples can be determined. Traditional methods can be used to determine the trait. For example, visual inspection of a region between the 12th and 13th rib of a beef carcass can be performed to determine the quality grade of meat obtained from the bovine subject whose nucleotide occurrences are identified. As will be understood, statistical methods can then be used to identify associations between the nucleotide occurrences and the trait. Accordingly, methods of the present invention enables a correlation between carcass value and genetic variation, so as to help identify superior genetic types for future breeding or cloning and management purposes, and to identify management practices that will maximize the value of the arrival in the market.

In another aspect, the present invention provides a method for identifying a bovine gene associated with a trait that includes identifying a bovine single nucleotide polymorphism (SNP) that influences a trait, by analyzing a genome-wide bovine SNP map for association with the trait, wherein the SNP is found on a target region of a bovine chromosome. Genes present on the target region are then identified. The presence of a gene on the target region of the bovine chromosome indicates that the gene is a candidate gene for association with the trait. The candidate gene can then be analyzed using methods known in the art to determine whether it is associated with the trait.

In another aspect, the present invention provides a method for identifying a breed of a bovine subject. The method includes identifying a nucleotide occurrence of a bovine single nucleotide polymorphism (SNP) from a nucleic acid sample of the subject, wherein the nucleotide occurrence is associated with the breed of the subject. The method typically includes identifying nucleotide occurrences of at least two SNPs from the nucleic acid sample, wherein the nucleotide occurrences are associated with the breed of the subject.

In another aspect, the present invention provides a system for determining the nucleotide occurrences at a population of bovine single nucleotide polymorphisms (SNPs). The system typically includes a hybridization medium and/or substrate that includes at least two oligonucleotides of the present invention, or oligonucleotides used in the methods of the present invention. For example, a solid support can be provided, to which a series of oligonucleotides can be directly or indirectly attached. In another aspect, a homogeneous assay is included in the system. In another aspect, a microfluidic device is included in the system. The hybridization medium or substrates are used to determine the nucleotide occurrence of bovine SNPs that are associated with a trait.

Accordingly, the oligonucleotides are used to determine the nucleotide occurrence of bovine SNPs that are associated with a trait. The determination can be made by selecting oligonucleotides that bind at or near a genomic location of each SNP of the series of bovine SNPs. The system of the present invention typically includes a reagent handling mechanism that can be used to apply a reagent, typically a liquid, to the solid support. The binding of an oligonucleotide of the series of oligonucleotides to a polynucleotide isolated from a genome can be affected by the nucleotide occurrence of the SNP. The system can include a mechanism effective for moving a solid support and a detection mechanism. The detection method detects binding or tagging of the oligonucleotides.

Medium to high-throughput systems for analyzing SNPs, known in the art such as the SNPStream® UHT Genotyping System (Beckman/Coulter, Fullerton, Calif.) (Boyce-Jacino and Goelet Patents), the Mass Array™ system (Sequenom, San Diego, Calif.) (Storm, N. et al. (2002) *Methods in Molecular Biology*. 212: 241-262.), the BeadArray™ SNP genotyping system available from Illumina (San Diego, Calif.) (Oliphant, A., et al. (June 2002) (supplement to Biotechniques), and TaqMan™ (Applied Biosystems, Foster City, Calif.) can be used with the present invention. However, the present invention provides a medium to high-throughput system that is designed to detect nucleotide occurrences of bovine SNPs, or a series of bovine SNPs that can make up a series of haplotypes. Therefore, as indicated above the system includes a solid support or other method to which a series of oligonucleotides can be associated that are used to determine a nucleotide occurrence of a SNP for a series of bovine SNPs that are associated with a trait. The system can further include a detection mechanism for detecting binding of the series of oligonucleotides to the series of SNPs. Such detection mechanisms are known in the art.

The system can be a microfluidic device. Numerous microfluidic devices are known that include solid supports with microchannels (See e.g., U.S. Pat. Nos. 5,304,487, 5,110745, 5,681,484, and 5,593,838).

The SNP detection systems of the present invention are designed to determine nucleotide occurrences of one SNP or a series of SNPs. The systems can determine nucleotide occurrences of an entire genome-wide high-density SNP map.

Numerous methods are known in the art for determining the nucleotide occurrence for a particular SNP in a sample. Such methods can utilize one or more oligonucleotide probes or primers, including, for example, an amplification primer pair that selectively hybridizes to a target polynucleotide, which corresponds to one or more bovine SNP positions. Oligonucleotide probes useful in practicing a method of the invention can include, for example, an oligonucleotide that is complementary to and spans a portion of the target polynucleotide, including the position of the SNP, wherein the presence of a specific nucleotide at the position (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe.

An oligonucleotide ligation assay (Grossman, P. D. et al. (1994) *Nucleic Acids Research* 22:4527-4534) also can be used to identify a nucleotide occurrence at a polymorphic position, wherein a pair of probes that selectively hybridize upstream and adjacent to and downstream and adjacent to the site of the SNP, and wherein one of the probes includes a terminal nucleotide complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the SNP site. An example of this type of assay is the SNPlex System (Applied Biosystems, Foster City, Calif.).

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP site can be useful, wherein the amplification product is examined to determine the nucleotide occurrence at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP locus can be sequenced using traditional sequence methodologies (e.g., the "dideoxy-mediated chain termination method," also known as the "Sanger Method"(Sanger, F., et al., *J. Molec. Biol.* 94:441 (1975); Prober et al. *Science* 238:336-340 (1987)) and the "chemical degradation method," "also known as the "Maxam-Gilbert method"(Maxam, A. M., et al., *Proc. Natl. Acad. Sci.* (U.S.A.) 74:560 (1977)), both references herein incorporated by reference) to determine the nucleotide occurrence at the SNP locus.

Methods of the invention can identify nucleotide occurrences at SNPs using genome-wide sequencing or "microsequencing" methods. Whole-genome sequencing of individuals identifies all SNP genotypes in a single analysis. Microsequencing methods determine the identity of only a single nucleotide at a "predetermined" site. Such methods have particular utility in determining the presence and identity of polymorphisms in a target polynucleotide. Such microsequencing methods, as well as other methods for determining the nucleotide occurrence at a SNP locus are discussed in Boyce-Jacino, et al., U.S. Pat. No. 6,294,336, incorporated herein by reference, and summarized herein.

Microsequencing methods include the Genetic Bit™ Analysis method disclosed by Goelet, P. et al. (WO 92/15712, herein incorporated by reference). Additional, primer-guided, nucleotide incorporation procedures for assaying polymorphic sites in DNA have also been described (Kornher, J. S. et al, *Nucleic Acids Res.* 17:7779-7784 (1989); Sokolov, B. P., *Nucleic Acids Res.* 18:3671 (1990); Syvanen, A.-C., et al., *Genomics* 8:684-692 (1990); Kuppuswamy, M. N. et al., *Proc. Natl. Acad. Sci.* (U.S.A.) 88:1143-1147 (1991); Prezant, T. R. et al, *Hum. Mutat.* 1:159-164 (1992); Ugozzoli, L. et al., GATA 9:107-112 (1992); Nyren, P. et al., *Anal. Biochem.* 208:171-175 (1993); and Wallace, WO89/10414). These methods differ from Genetic Bit™ Analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al.

Amer. J. Hum. Genet. (1993) 52:46-59 Other formats for microsequencing include Pyrosequencing (Pyrosequencing AB, Uppsala, Sweden, Alderbom et al (2000) Genome Res. 10:1249-1258).

Alternative microsequencing methods have been provided by Mundy, C. R. (U.S. Pat. No. 4,656,127) and Cohen, D. et al (French Patent 2,650,840; PCT Appln. No. WO91/02087) which discusses a solution-based method for determining the identity of the nucleotide of a polymorphic site. As in the Mundy method of U.S. Pat. No. 4,656,127, a primer is employed that is complementary to allelic sequences immediately 3'-to a polymorphic site.

In response to the difficulties encountered in employing gel electrophoresis to analyze sequences, alternative methods for microsequencing have been developed. Macevicz (U.S. Pat. No. 5,002,867), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a set of probes has been tested.

Boyce-Jacino, et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target.

The occurrence of a SNP can be determined using denaturing HPLC such as described in Nairz K et al (2002) *Proc. Natl. Acad. Sci.* (U.S.A.) 99:10575-80, and the Transgenomic WAVE® System (Transgenomic, Inc. Omaha, Nebr.).

Oliphant et al. report a method that utilizes BeadArray™ Technology that can be used in the methods of the present invention to determine the nucleotide occurrence of a SNP (supplement to Biotechniques, June 2002). Additionally, nucleotide occurrences for SNPs can be determined using a DNAMassARRAY system (SEQUENOM, San Diego, Calif.). This system combines proprietary SpectroChips™, microfluidics, nanodispensing, biochemistry, and MALDI-TOF MS (matrix-assisted laser desorption ionization time of flight mass spectrometry).

As another example, the nucleotide occurrences of bovine SNPs in a sample can be determined using the SNP-IT™ method (Beckman Coulter, Fullerton, Calif.). In general, SNP-IT™ is a 3-step primer extension reaction. In the first step a target polynucleotide is isolated from a sample by hybridization to a capture primer, which provides a first level of specificity. In a second step the capture primer is extended from a terminating nucleotide triphosphate at the target SNP site, which provides a second level of specificity. In a third step, the extended nucleotide trisphosphate can be detected using a variety of known formats, including: direct fluorescence, indirect fluorescence, an indirect calorimetric assay, mass spectrometry, fluorescence polarization, etc. Reactions can be processed in 384 well format in an automated format using a SNPstream™ instrument (Beckman Coulter, Fullerton, Calif.). Reactions can also be analyzed by binding to Luminex biospheres (Luminex Corporation, Austin, Tex., Cai. H. (2000) Genomics 66(2):135-43.). Other formats for SNP detection include TaqMan™ (Applied Biosystems, Foster City, Calif.), Rolling circle (Hatch et al (1999) *Genet. Anal.* 15: 35-40; and Qi et al (2001) *Nucleic Acids Research* Vol. 29 e116), fluorescence polarization (Chen, X., et al. (1999) *Genome Research* 9:492-498), SNaPShot (Applied Biosystems, Foster City, Calif.; and Makridakis, N. M. et al. (2001) *Biotechniques* 31:1374-80), oligo-ligation assay (Grossman, P. D., et al. (1994) *Nucleic Acids Research* 22:4527-4534), locked nucleic acids (LNA™, Link, Technologies LTD, Lanarkshire, Scotland, EP patent 1013661, U.S. Pat. No. 6,268,490), Invader Assay (Aclara Biosciences, Wilkinson, D. (1999) *The Scientist* 13:16), padlock probes (Nilsson et al. *Science* (1994), 265: 2085), Sequence-tagged molecular inversion probes (similar to padlock probes) from ParAllele Bioscience (South San Francisco, Calif.; Hardenbol, P. et al. (2003) *Nature Biotechnology* 21:673-678), Molecular Beacons (Marras, S. A. et al. (1999 *Genet Anal.* 14:151-156), the READIT™ SNP Genotyping System from Promega (Madison, Wis.) (Rhodes R. B. et al. (2001) Mol Diagn. 6:55-61), Dynamic Allele-Specific Hybridization (DASH) (Prince, J. A. et al. (2001) *Genome Research* 11:152-162), the Qbead™ system (quantum dot encoded microspheres conjugated to allele-specific oligonucleotides)(Xu H. et al. (2003) *Nucleic Acids Research* 31:e43), Scorpion primers (similar to molecular beacons except unimolecular) (Thelwell, N. et al. (2000) *Nucleic Acids Research* 28:3752-3761), and Magiprobe (a novel fluorescence quenching-based oligonucleotide probe carrying a fluorophore and an intercalator)(Yamane A. (2002) *Nucleic Acids Research* 30:e97). In addition, Rao, K. V. N. et al. ((2003) *Nucleic Acids Research.* 31:e66), recently reported a microsphere-based genotyping assay that detects SNPs directly from human genomic DNA. The assay involves a structure-specific cleavage reaction, which generates fluorescent signal on the surface of microspheres, followed by flow cytometry of the microspheres. With a slightly different twist on the Sequenom technology (MALDI), Sauer et al. ((2003) *Nucleic Acids Research* 31:e63) generate charge-tagged DNA (post PCR and primer extension), using a photocleavable linker.

Accordingly, using the methods described above, the bovine haplotype allele or the nucleotide occurrence of a bovine SNP can be identified using an amplification reaction, a primer extension reaction, or an immunoassay. The bovine haplotype allele or bovine SNP can also be identified by contacting polynucleotides in the sample or polynucleotides derived from the sample, with a specific binding pair member that selectively hybridizes to a polynucleotide region comprising the bovine SNP, under conditions wherein the binding pair member specifically binds at or near the bovine SNP. The specific binding pair member can be an antibody or a polynucleotide.

The nucleotide occurrence of a SNP can be identified by other methodologies as well as those discussed above. For example, the identification can use microarray technology, which can be performed with or without PCR, or sequencing methods such as mass spectrometry, scanning electron microscopy, or methods in which a polynucleotide flows past a sorting device that can detect the sequence of the polynucleotide. The occurrence of a SNP can be identified using electrochemical detection devices such as the eSensor™ DNA detection system (Motorola, Inc., Yu, C. J. (2001) *J. Am Chem. Soc.* 123:11155-11161). Other formats include melting curve analysis using fluorescently labeled hybridization probes, or intercalating dyes (Lohmann, S. (2000) *Biochemica* 4, 23-28, Herrmann, M. (2000) Clinical Chemistry 46: 425).

The SNP detection systems of the present invention typically utilize selective hybridization. As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying a nucleotide occurrence of a SNP. It will be recognized that some amount of non-specific hybridization is unavoidable, but is acceptable provide that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42EC (moderate stringency conditions); and 0.1×SSC at about 68EC (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 15 nucleotides in length, usually at least about 18 nucleotides, and particularly about 21 nucleotides or more in length.

A polynucleotide can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucleic Acids Research* (1994) 22:5220-5234 Jellinek et al., *Biochemistry* (1995) 34:11363-11372; Pagratis et al., *Nature Biotechnol.* (1997) 15:68-73, each of which is incorporated herein by reference). Primers and probes can also be comprised of peptide nucleic acids (PNA) (Nielsen PE and Egholm M. (1999) *Curr. Issues Mol. Biol.* 1:89-104).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res*. (1994) 22:977-986, Ecker and Crooke, *BioTechnology* (1995) 13:351360, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide or oligonucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). Thus, the term polynucleotide as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR).

A method of the identifying a SNP also can be performed using a specific binding pair member. As used herein, the term "specific binding pair member" refers to a molecule that specifically binds or selectively hybridizes to another member of a specific binding pair. Specific binding pair member include, for example, probes, primers, polynucleotides, antibodies, etc. For example, a specific binding pair member includes a primer or a probe that selectively hybridizes to a target polynucleotide that includes a SNP loci, or that hybridizes to an amplification product generated using the target polynucleotide as a template.

As used herein, the term "specific interaction," or "specifically binds" or the like means that two molecules form a complex that is relatively stable under physiologic conditions. The term is used herein in reference to various interactions, including, for example, the interaction of an antibody that binds a polynucleotide that includes a SNP site; or the interaction of an antibody that binds a polypeptide that includes an amino acid that is encoded by a codon that includes a SNP site. According to methods of the invention, an antibody can selectively bind to a polypeptide that includes a particular amino acid encoded by a codon that includes a SNP site. Alternatively, an antibody may preferentially bind a particular modified nucleotide that is incorporated into a SNP site for only certain nucleotide occurrences at the SNP site, for example using a primer extension assay.

A specific interaction can be characterized by a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or greater. A specific interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. Methods for determining whether two molecules interact specifically are well known and include, for example, equilibrium dialysis, surface plasmon resonance, and the like.

The invention also relates to kits, which can be used, for example, to perform a method of the invention. Thus, in one embodiment, the invention provides a kit for identifying nucleotide occurrences or haplotype alleles of bovine SNPs. Such a kit can contain, for example, an oligonucleotide probe, primer, or primer pair, or combinations thereof. Such oligonucleotides being useful, for example, to identify a SNP or haplotype allele as disclosed herein; or can contain one or more polynucleotides corresponding to a portion of a bovine gene containing one or more nucleotide occurrences associated with a bovine trait, such polynucleotide being useful, for example, as a standard (control) that can be examined in parallel with a test sample. In addition, a kit of the invention can contain, for example, reagents for performing a method of the invention, including, for example, one or more detectable labels, which can be used to label a probe or primer or can be incorporated into a product generated using the probe or primer (e.g., an amplification product); one or more polymerases, which can be useful for a method that includes a primer extension or amplification procedure, or other enzyme or enzymes (e.g., a ligase or an endonuclease), which can be useful for performing an oligonucleotide ligation assay or a mismatch cleavage assay; and/or one or more buffers or other reagents that are necessary to or can facilitate performing a method of the invention. The primers or probes can be included in a kit in a labeled form, for example with a label such as biotin or an antibody.

In one embodiment, a kit of the invention provides a plurality of oligonucleotides of the invention, including one or more oligonucleotide probes or one or more primers, including forward and/or reverse primers, or a combination of such probes and primers or primer pairs. Such a kit also can contain probes and/or primers that conveniently allow a method of the invention to be performed in a multiplex format.

The kit can also include instructions for using the probes or primers to determine a nucleotide occurrence of at least one bovine SNPs.

In another aspect, the present invention provides a computer system that includes a database having records containing information regarding a series of bovine single nucleotide polymorphisms (SNPs), and a user interface allowing a user to input nucleotide occurrences of the series of bovine SNPs for a bovine subject. The user interface can be used to query the database and display results of the query. The database can include records representing some or all of the SNP of a bovine SNP map, such as a high-density bovine SNP map. The database can also include information regarding haplotypes and haplotype alleles from the SNPs. Furthermore, the database can include information regarding traits and/or traits that are associated with some or all of the SNPs and/or haplotypes. In these embodiments the computer system can be used, for example, for any of the aspects of the invention that infer a trait of a bovine subject.

The computer system of the present invention can be a stand-alone computer, a conventional network system including a client/server environment and one or more database servers, and/or a handheld device. A number of conventional network systems, including a local area network (LAN) or a wide area network (WAN), are known in the art. Additionally, client/server environments, database servers, and networks are well documented in the technical, trade, and patent literature. For example, the database server can run on an operating system such as UNIX, running a relational database management system, a World Wide Web application, and a World Wide Web Server. When the computer system is a handheld device it can be a personal digital assistant (PDA) or another type of handheld device, of which many are known.

Typically, the database of the computer system of the present invention includes information regarding the location and nucleotide occurrences of bovine SNPs. Information regarding genomic location of the SNP can be provided for example by including sequence information of consecutive sequences surrounding the SNP, that only 1 part of the genome provides 100% match, or by providing apposition number of the SNP with respect to an available sequence entry, such as a Genbank sequence entry, or a sequence entry for a private database, or a commercially licensed database of DNA sequences. The database can also include information regarding nucleotide occurrences of SNPs, since as discussed herein typically nucleotide occurrences of less than all four nucleotides occur for a SNP.

The database can include other information regarding SNPs or haplotypes such as information regarding frequency of occurrence in a bovine population. Furthermore, the database can be divided into multiple parts, one for storing sequences and the others for storing information regarding the sequences. The database may contain records representing additional information about a SNP, for example information identifying the gene in which a SNP is found, or nucleotide occurrence frequency information, or characteristics of the library or clone which generated the DNA sequence, or the relationship of the sequence surrounding the SNP to similar DNA sequences in other species.

The parts of the database of the present invention can be flat file databases or relational databases or object-oriented databases. The parts of the database can be internal databases, or external databases that are accessible to users. An internal database is a database maintained as a private database, typically maintained behind a firewall, by an enterprise. An external database is located outside an internal database, and is typically maintained by a different entity than an internal database. A number of external public biological sequence databases, particularly SNP databases, are available and can be used with the current invention. For example, the dbSNP database available from the National Center for Biological Information (NCBI), part of the National Library of Medicine, can be used with the current invention to provide comparative genomic information to assist in identifying bovine SNPs.

In another aspect, the current invention provides a population of information regarding bovine SNPs and haplotypes. The population of information can include an identification of traits associated with the SNPs and haplotyopes. The population of information is typically included within a database, and can be identified using the methods of the current invention. The population of sequences can be a subpopulation of a larger database, that contains only SNPs and haplotypes related to a particular trait. For example, the subpopulation can be identified in a table of a relational database. A population of information can include all of the SNPs and/or haplotypes of a genome-wide SNP map.

In addition to the database discussed above, the computer system of the present invention includes a user interface capable of receiving entry of nucleotide occurrence information regarding at least one SNP. The interface can be a graphic user interface where entries and selections are made using a series of menus, dialog boxes, and/or selectable buttons, for example. The interface typically takes a user through a series of screens beginning with a main screen. The user interface can include links that a user may select to access additional information relating a bovine SNP map.

The function of the computer system of the present invention that carries out the trait inference methods typically includes a processing unit that executes a computer program product, itself representing another aspect of the invention, that includes a computer-readable program code embodied on a computer-usable medium and present in a memory function connected to the processing unit. The memory function can be ROM or RAM.

The computer program product, itself another aspect of the invention, is read and executed by the processing unit of the computer system of the present invention, and includes a computer-readable program code embodied on a computer-usable medium. The computer-readable program code relates to a plurality of sequence records stored in a database. The sequence records can contain information regarding the relationship between nucleotide occurrences of a series of bovine single nucleotide polymorphisms (SNPs) and a trait of one or more traits. The computer program product can include computer-readable program code for providing a user interface capable of allowing a user to input nucleotide occurrences of the series of bovine SNPs for a bovine subject, locating data corresponding to the entered query information, and displaying the data corresponding to the entered query. Data corresponding to the entered query information is typically located by querying a database as described above.

In another embodiment of the present invention, the computer system and computer program products are used to perform bioeconomic valuations used to perform methods described herein, such as methods for estimating the value of a bovine subject or meat that will be obtained therefrom.

The following examples are intended to illustrate but not limit the invention.

EXAMPLE 1

Generation of a High-density Bovine Genetic SNP Map

This example illustrates the generation of a high density bovine genetic SNP map created through a whole genome sequencing of the bovine genome using the shotgun sequencing approach. This approach was selected to provide hundreds of thousands of SNP markers, as described by Venter, J. C, et al., (Science 291:1304-1351 (2001), in order to perform a whole-genome association study with adequate density of markers to ensure discovery of markers in disequilibrium with mutations influencing the targeted traits.

Shotgun sequencing was performed with four different bovine individuals that represented different breed types. The shotgun sequencing was performed according to the methods of Venter, J. C, et al., (Science 291:1304-1351 (2001)). By this method, random fragments of bovine sequence were generated and size selected to 2.5 and 10 kb. These fragments of bovine DNA were inserted into a sequencing vector to create high quality plasmid libraries suitable for high throughput sequencing.

Shotgun sequencing was performed with four different bovine subjects that represented several different breed types: Angus, Limousin, Brahman and Simmental. Upon whole genome assembly of the sequenced fragments, contigs were formed from consensus sequence, and sequence variants were identified and cataloged. 786,777 sequence variants that differed by a single nucleotide became candidate SNP markers for the high-density SNP map. The relative position of each candidate SNP within the bovine genome was determined using the assembled human genome as scaffolding creating a candidate map of 242,181 human-mapped markers. Upon positioning of the SNPs within the genome, individual markers were tested to determine informativeness within the cattle population using 210 animals representing diverse breeds (Angus, Charolais, Limousin, Hereford, Brahman, Simmental and Gelbvieh) and Mendialian segregation (21 trios of parents and progeny). Selected markers were polymorphic in the majority of the breeds tested. Any markers within a region that failed the test were discarded and replaced with another marker in the region. These markers were also validated against the test population. This process was repeated until a relatively evenly distributed genetic SNP map was obtained, where the average genetic distance between any two adjacent markers is 0.5 cM.

EXAMPLE 2

Identification of Bovine SNPS Associated with Tenderness, Fat, Marbling, Yield, and/or Daily Gain This example illustrates the identification of SNPs from the high-density bovine SNP map identified in Example 1, that are associated with the traits meat tenderness, fat thickness, marbling, yield, and/or daily gain.

DNA samples from bovine subjects were obtained by collecting 50 ml of whole blood from the 4,791 bovine subjects. 25 ml of whole blood was used for DNA extraction using standard methods and concentrations of DNA were calculated using standard fluorimetric methods. Animals representing less than or equal to the 10th percentile of low numeric phenotypic animals (44 individuals) and the 90th percentile and greater of high phenotypic animals (44 individuals) were identified for each trait. The low numeric values were identified as "Low" and the high numeric values were identified as "High". DNA samples were pooled from bovine individuals that represent high and low phenotypic extremes for the expression of a target trait in a population of bovine animals with each of the 44 animals contributing equally to the pool of DNA. A separate "High" and "Low" pool was created for each biological type (English, Continental, and Brahman crosses) by treatment group (Early, Optimum, Late) for each of the five traits resulting in 90 total pools. In addition to the 90 pools listed above, another group was formed based on animals that were 5 standard deviations above the mean for numeric tenderness values. Eleven animals were included in this group of individuals and the pool was compared to the other tenderness groups resulting in a total of 91 pools. Each pool was tested against each of the 6189 mapped and validated SNP markers. The SNP detection platform utilized in the experiment was the Beckman Coulter SNP-IT system, utilizing single-base extension of the SNP base. Allele frequency was estimated for each pool based on the fluorescence intensity of each of the two incorporated fluorescent labels corresponding to the SNP alleles. These estimates were adjusted for marker specific characteristics and incorporation differences. A test statistic was developed based on a Chi-square distribution of differences among allele frequencies of the high minus low pools. These test statistics were summed across the 9 breed by treatment groups within each trait resulting in Chi-square distribution. SNP markers reaching a threshold test statistic of 46.96294 for the trait of tenderness and 21.66599 ($p<0.01$) for the remaining four traits of retail yield, daily gain, fat thickness and marbling were identified as associated SNPs and are listed in Tables 1A and 1B.

The high-density SNP map was used to identify SNPs that are associated with a series of bovine traits. The traits included marbling, tenderness, fat thickness, yield, and daily gain. Tables 1A and 1B (filed herewith on a compact disc) provide the identity of SNPs that associated with one or more of the traits analyzed. Twenty five hundred and ten associated SNPs were identified for all five traits.

Table 1A provides the following information, from left to right columns: SNP name; a sequence identifier of the sequence listing filed herewith, for an amplicon, wherein the SNP position is position 300 of the amplicon; position of the SNP within the amplicon (i.e. position 300); The nucleotide sequence and SEQ ID NO: for an extension primer capable of priming polynucleotide synthesis across the SNP position; trait(s) that are associated with the SNP; Characteristics of the trait that are associated with specific nucleotide occurrences at the SNP; Nucleotide occurrences that have been detected at the SNP position; And the sequence identifier of contig sequences that are located within 500,000 nucleotides from the SNP on the bovine genome. Table 1B provides the following information from left to right columns: SNP name; A sequence name of a contig that includes the SNP position, as well as the position numbers within the contig for an amplicon that includes the SNP; Position of the SNP within the amplicon (i.e. position 300); The nucleotide sequence for an extension primer capable of priming polynucleotide synthesis across the SNP position; trait(s) that are associated with the SNP; Characteristics of the trait that are associated with specific nucleotide occurrences at the SNP; Nucleotide occurrences that have been detected at the SNP position; And the sequence identifier of contig sequences that are located within 500,000 nucleotides from the SNP on the bovine genome.

EXAMPLE 3

Determination of the Distance of Disequilibrium in Cattle

This example utilizes a few of the associated SNPs disclosed in Example 2, to identify additional SNPs that are associated with the same traits, using the physical proximity on the genome of the SNPs. Furthermore, the results are used to calculate a distance of disequilibrium in cattle. In this example, "shear force" is used to refer to tenderness, "vision retail yield" is used to refer to retail yield, and "average daily gain" is used to refer to daily gain.

In the past 10 years numerous methods have been developed to identify alleles associated with phenotypic effects, traits or diseases. Linkage disequilibrium and measures of linkage disequilibrium have been of particular interest for studies of complex traits or diseases (see reviews L. R. Cardon and J. I. Bell, "Association study Designs for Complex Diseases", Nature Reviews/Genetics 2:91-99 (2001); N. A. Rosenberg and M. Nordborg "Genealogical Trees, Coalescent Theory and the analysis of Genetic Polymorphisms", Nature Reviews/Genetics 3:380-390, 2002). LD occurs where blocks or regions of neighboring markers are co-inherited from a common ancestor. The degree of LD varies considerably throughout the genome and is a function of time, recombination events, mutation rate and population structure. The extent of LD can vary from a few thousand base pairs to several centimorgans. This has been most extensively documented in human studies (K. W. Broman and J. L. Weber. "Long homozygous chromosomal segments in the CEPH families". Am. J. Hum. Genet. 65:1493-1500 (1999); A. G. Clark, K. M. Weiss, D. A. Nickerson, et. al. "Haplotype structure and population genetic inferences from nucleotide-sequence variation in human lipoprotein lipase. Am. J. Hum. Genet. 63:595-612 (1999); D. Reich, M. Cargill, S. Bolk, et al., "Linkage disequilibrium in the human genome". Nature 411:199-204 (2001); J. Stephens, J. A. Schneider, D. A. Tanguay, et al., "Haplotype variation and linkage disequilibrium in 313 human genes". Science 293:489-493 (2001); E. Dawson, GR Abecasis, S. Bumpstead, et al "A first generation linkage disequilibrium map of human chromosome 22". Nature 418(6897):544-548 (2002); S B Gabriel, S F Schaffner, H Nguyen, et al. "The structure of haplotype blocks in the human genome" Science 296: 225-2229 (2002)). Similar results have been observed in other species including cattle (F. Farnir, W. Coppieters, J-J. Arranz, et. al., "Extensive Genome-wide Linkage Disequibibrium in Cattle" Genome Research 10:220-227 (2000)). These studies and others have also shown that a SNP or multiple SNPs associated with a phenotype can be used as predictive of gene(s) causing differences in trait phenotypes within a region of high LD although they may or may not be the precise causative gene (as further examples, see also: A. M. Glazier, J H Nadeau and T J Aitman, "Finding Genes that Underlie Complex Traits" Science 298: 2345-2348 (2002); M. Blumenfield, et al. U.S. Pat. No. 6,531,279; A, Hovnanian, et al., U.S. Pat. Pub. No. 20030190637A1; M. Blumenfield, et al. U.S. Pat. No. 6,528,260; M. R. Hayden, et al. U.S. Pat. No. 6,617,122; C. M. Drysdale, et al. U.S. Pat. No. 6,586,183; M. Galvin, et al., U.S. Pat. No. 6,586,175; L. Bougueleret, et al., U.S. Pat. No. 6,582,909; S. Van Dijk, et al., U.S. Pat. No. 6,558,905. A. E. Anastasio, et al., U.S. Pat. No. 6,521,741). While it has been established that markers can be identified that associate with a specific trait, and, therefore, become diagnostic for the trait, the distance that disequilibrium reaches has not been determined in cattle with a dense marker map. Therefore, an experiment to determine the disequilibrium distance in cattle was performed using the high-density SNP map disclosed in Example 1.

The high-density SNP map disclosed in Example 1 was used to identify SNPs that are in physical proximity to a few of the associated SNPs disclosed in Example 2. Nucleotide occurrences of the SNPs were determined using the method disclosed in Example 2. A determination of whether on-test SNPs was associated with a trait was performed as disclosed in Example 2.

As discussed above, the study was performed to verify the assumption that markers that are in close physical proximity on the bovine genome will associate with the same trait(s) because markers in linkage disequilibrium with the associated SNP marker will also be in linkage disequilibrium with the mutation(s) influencing the trait.

As indicated in Table 2, SNP3 (MMBT22302) is significantly associated with the trait of average daily gain ("ADG" in Table 2). Several SNPs were identified using the high-density SNP map of Example 1 that are located at various distances from SNP3 on the bovine genome (Table 2). For example, SNP2 is 466,047 nucleotides from SNP3. Furthermore, SNP5 was identified which is 408,732 nucleotides from SNP3. SNP6 was identified which is 1.0 million nucleotides from SNP3. Finally, SNP4 was identified, which is 308,742 nucleotides.

As illustrated in Table 2, SNPs that were located within 500,000 nucleotides of SNP3 also were associated with average daily gain, whereas those that were located greater than 500,000 nucleotides from SNP3 were not associated with average daily gain. For example, linkage disequilibrium reaches 466,047 bases to SNP2, but not to SNP1 at 1.5 Mb; linkage disequilibrium reaches to 408,732 bases to SNP5, but not to SNP6 at 1.0 Mb. SNP4, which is 308,742 nucleotides from SNP3, was discovered by sequencing the contig of DNA that maps to this region in 4 different breeds of cattle. It is also in disequilibrium with average daily gain.

TABLE 2

Disequilibrium analysis in relation to SNP distance from MMBT22302.

|   | SNP | At Position 300 in SEQ ID NO | Marker Association P < .01 Trait | Human Chromosome Location | bp location | Difference from MMBT22302 |
|---|---|---|---|---|---|---|
| 1 | MMBT22310 | not in patent | Not Sign | HC16 | 45425130 | 1,507,460 |
| 2 | MMBT13976 | 20291 | ADG | HC16 | 46466543 | 466,047 |
| 3 | MMBT22302 | 19666 | ADG | HC16 | 46932590 | |
| 4 | MMBT09532 | 21944 | ADG | HC16 | 47241332 | 308,742 |
| 5 | MMBT09533 | 19999 | ADG | HC16 | 47341322 | 408,732 |
| 6 | MMBT09535 | 21078 | Not Sign | HC16 | 47958246 | 1,025,656 |

To further analyze linkage disequilibrium, a similar analysis was performed using another SNP identified as an associated SNP in Example 2. SNP9 (MMBT03905) is significantly associated with vision retail yield (VRY). SNPs 7-8 and 10-12 were identified that are various distances from SNP9 (Table 2). Again, SNPs that were located less than or equal to about 500,000 nucleotides from the associated SNP, were also associated with the trait, whereas those that were present greater than 500,000 nucleotides from a known associated SNP, were not associated. For example, SNPs 8 and 11 were identified as also being highly significantly associated with VRY and are located less than 500,000 bp from SNP9. (Table 3). On the other hand, SNPs 7 and 12, which are greater than 500,000 bp from SNP9, were not associated with the trait. Furthermore, through additional sequencing, SNP10 was discovered and also found to be in linkage disequilibrium with VRY.

The results of this Example indicate that disequilibrium in cattle exists across the region of 500,000 nucleotides from an associated SNP, in each direction. Therefore, it is expected that when an associated SNP is identified, other markers within this 500,000 bp region will also be in disequilibrium with the associated SNP and with the trait of interest, and can be used to infer associations with the trait of interest.

Although the invention has been described with reference to the above examples, it will be understood that modifications and variations are encompassed within the spirit and scope of the invention. Accordingly, the invention is limited only by the following claims.

TABLE 3

Disequilibrium analysis in relation to SNP distance from MMBT3905.

| | SNP | At Position 300 in SEQ ID NO | Marker Association P < .01 Trait | Human Chromosome Location | bp location | Difference from MMBT03905 |
|---|---|---|---|---|---|---|
| 7 | MMBT12437 | not in patent | Not Sign | HC04 | 177035705 | 518426 |
| 8 | MMBT03904 | 20327 | VRY | HC04 | 177201331 | 352800 |
| 9 | MMBT03905 | 19816 | VRY | HC04 | 177554131 | |
| 10 | MMBT03906 | 20240 | VRY | HC04 | 177900170 | 346039 |
| 11 | MMBT05906 | 20045 | VRY | HC04 | 178047550 | 493419 |
| 12 | MMBT03907 | not in patent | Not Sign | HC04 | 178113631 | 559500 |

As indicated in Tables 1A and 1B, SNP16 (MMBT02782) is highly significantly associated with shear force (SHF, Table 4). SNPs 14, 15, 17 and 18 were identified which are located within 500,000 nucleotides of SNP16 (Table 4). Once again, all of these SNPs, which are within 500,000 nucleotides of an associated SNP, were found to be associated with the same trait. That is, SNPs 14, 15, 17, and 18 were all found to be associated with SHF (Table 4). On the other hand, SNPs 1 and 7, which are located beyond 1.0 million nucleotides from SNP16, were not associated with SHF.

TABLE 4

Disequilibrium analysis in relation to SNP distance from MMBT02782.

| | SNP | At Position 300 in SEQ ID NO | Marker Association P < .01 Trait | Human Chromosome Location | bp location | Difference from MMBT02782 |
|---|---|---|---|---|---|---|
| 13 | MMBT02777 | 19767 | Not Sign | HC04 | 46401363 | 1594271 |
| 14 | MMBT02781 | 20791 | SHF | HC04 | 47777758 | 217876 |
| 15 | MMBT19460 | 20790 | SHF | HC04 | 47778002 | 217632 |
| 16 | MMBT02782 | 20901 | SHF | HC04 | 47995634 | |
| 17 | MMBT03688 | 20765 | SHF | HC04 | 48379141 | 383507 |
| 18 | MMBT02784 | 20764 | SHF | HC04 | 48492482 | 496848 |
| 19 | MMBT02786 | not in patent | Not Sign | HC04 | 49190953 | 1195319 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07468248B2). An electronic copy of the "Sequence Listing" will also be available from the USPTO upon request and payment of the fee set forth in 37 CFR 1.19(b)(3).

What is claimed is:

1. A method for inferring a trait of a bovine subject from a nucleic acid sample of the bovine subject, comprising identifying in the nucleic acid sample, a nucleotide occurrence of a single nucleotide polymorphism (SNP) at position 300 of SEQ ID NO:21645, thereby inferring the trait, wherein the trait is marbling, tenderness, fat thickness, red meat yield, or average daily weight gain.

2. The method of claim 1, wherein the nucleotide occurrence of at least 2 SNPs is determined to infer the trait, wherein one of the SNPs is at position 300 of SEQ ID NO:21645 and the remaining SNP or SNPs are at position 300 of any of SEQ ID NO:19473 to SEQ ID NO:21644, or SEQ ID NO:21646 to SEQ ID NO:21982.

3. The method of claim 2, wherein the nucleotide occurrences of at least 2 SNPs comprise a haplotype allele, and wherein the method infers the trait using the identified haplotype allele.

4. The method of claim 2, wherein at least 2 SNPs are related by dominance and/or epistasis.

5. The method of claim 4, further comprising identifying a diploid pair of haplotype alleles and inferring the trait using the diploid pair of haplotype alleles.

6. The method of claim 2, wherein the remaining SNP or SNPs is associated with a trait selected from the group consisting of marbling, tenderness, quality grade, muscle content, fat thickness, feed efficiency, red meat yield, average daily weight gain, disease resistance, disease susceptibility, feed intake, protein content, bone content, maintenance energy requirement, mature size, amino acid profile, fatty acid profile, milk production, a milk quality susceptibility to the buller syndrome, stress susceptibility and response, temperament, digestive capacity, production of calpain, caplastatin and myostatin, pattern of fat deposition, ribeye area, fertility, ovulation rate, conception rate, and susceptibility to infection with and shedding of pathogens.

7. The method of claim 2, wherein the trait is fat thickness.

8. The method of claim 7, wherein at least one SNP and at least one nucleotide occurrence are selected from at least one of the SNPs and nucleotide occurrences indicated in Table 1A as associated with high fat thickness.

9. The method of claim 7, wherein at least one SNP and at least one nucleotide occurrence are selected from at least one of the SNPs and nucleotide occurrences indicated in Table 1A as associated with low fat thickness.

10. The method of claim 2, wherein the trait is retail yield.

11. The method of claim 10, wherein at least one SNP and at least one nucleotide occurrence are selected from at least one of the SNPs and nucleotide occurrences indicated in Table 1A as associated with high retail yield.

12. The method of claim 10, wherein at least one SNP and at least one nucleotide occurrence are selected from at least one of the SNPs and nucleotide occurrences indicated in Table 1A as associated with low retail yield.

13. The method of claim 2, wherein the trait is tenderness.

14. The method of claim 13, wherein at least one SNP and at least one nucleotide occurrence are selected from at least one of the SNPs and nucleotide occurrences indicated in Table 1A as associated with high tenderness.

15. The method of claim 13, wherein at least one SNP and at least one nucleotide occurrence are selected from at least one of the SNPs and nucleotide occurrences indicated in Table 1A as associated with low tenderness.

16. The method of claim 2, wherein the trait is marbling.

17. The method of claim 16, wherein at least one SNP and at least one nucleotide occurrence are selected from at least one of the SNPs and nucleotide occurrences indicated in Table 1A as associated with more abundant marbling.

18. The method of claim 16, wherein at least one SNP and at least one nucleotide occurrence are selected from at least one of the SNPs and nucleotide occurrences indicated in Table 1A as associated with less abundant marbling.

19. The method of claim 2, wherein the trait is average daily gain.

20. The method of claim 19, wherein at least one SNP and at least one nucleotide occurrence are selected from at least one of the SNPs and nucleotide occurrences indicated in Table 1A as associated with a high daily gain.

21. The method of claim 19, wherein at least one SNP and at least one nucleotide occurrence are selected from at least one of the SNPs and nucleotide occurrences indicated in Table 1A as associated with low daily gain.

22. A method for determining a nucleotide occurrence of a polymorphism in a bovine sample, comprising:

a) contacting a bovine polynucleotide in the sample with an oligonucleotide that binds to a target region, wherein the target region comprises a position at position 300 of SEQ ID NO:21645 or wherein the target region is within 3000 nucleotides of a nucleotide at position 300 of SEQ ID NO:21645, and b) determining the nucleotide occurrence of a single nucleotide polymorphism (SNP) at position 300 of SEQ ID NO:21645, wherein the determination comprises analyzing binding of the oligonucleotide or detecting an amplification product generated using the oligonucleotide, thereby determining the nucleotide occurrence of the polymorphism.

23. The method of claim 22, wherein the oligonucleotide binds to a target sequence that comprises a single nucleotide polymorphism (SNP) at position 300 of SEQ ID NO:21645 and the nucleotide occurrence is determined based on the binding of the oligonucleotide to the target sequence.

24. The method of claim 22, wherein the bovine polynucleotide is contacted with a pair of oligonucleotides that comprise a primer pair, and the nucleotide occurrence is determined using an amplification product generated using the primer pair.

25. The method of claim 22, wherein the terminal nucleotide of the oligonucleotide binds to the SNP.

26. The method of claim 24, wherein the polynucleotide is contacted with a pair of oligonucleotides each comprising a different detectable label.

27. The method of claim 26, wherein the terminal nucleotide of each oligonucleotide pair is complementary to a different nucleotide at position 300 of SEQ ID NO:21645, or a complement thereof.

28. A method for identifying a bovine single nucleotide polymorphism (SNP) associated with a trait, comprising identifying a test SNP that is in disequilibrium with a SNP position at position 300 of SEQ ID NO:21645.

29. The method of claim 28, wherein the test SNP is in a target region of a bovine genome, wherein the target region is within about 500,000 nucleotides from a SNP position at position 300 of SEQ ID NO:21645.

30. The method of claim 29, wherein the target region consists of at least 20 contiguous nucleotides of SEQ ID NOS:24493 to 64886.

31. The method of claim 29, wherein the target region consists of at least 20 contiguous nucleotides of SEQ ID NOS:19473 to 21982.

32. The method of claim 28, wherein the trait is marbling, tenderness, quality grade, muscle content, fat thickness, feed efficiency, red meat yield, average daily weight gain, disease resistance, disease susceptibility, feed intake, protein content, bone content, maintenance energy requirement, mature size, amino acid profile, fatty acid profile, milk production, a milk quality susceptibility to the buller syndrome, stress susceptibility and response, temperament, digestive capacity, production of calpain, caplastatin and myostatin, pattern of fat deposition, ribeye area, fertility, ovulation rate, conception rate, or susceptibility to infection with and shedding of pathogens.

33. The method of claim 32, wherein the trait is fat thickness, retail yield, tenderness, marbling, or average daily gain.

* * * * *

UNITED STATES PATENT AND TRADEMARK OFFICE
CERTIFICATE OF CORRECTION

| | | |
|---|---|---|
| PATENT NO. | : 7,468,248 B2 | Page 1 of 1 |
| APPLICATION NO. | : 10/750623 | |
| DATED | : December 23, 2008 | |
| INVENTOR(S) | : Sue K. DeNise et al. | |

It is certified that error appears in the above-identified patent and that said Letters Patent is hereby corrected as shown below:

In the Specification:

In Columns 41 and 42, please insert the following page-wide LENGTHY TABLES statement so that it immediately precedes the page-wide SEQUENCE LISTING statement:

---

LENGTHY TABLES

The patent contains a lengthy table section. A copy of the table is available in electronic form from the USPTO web site (http://seqdata.uspto.gov/?pageRequest=docDetail&DocID=US07468248B2). An electronic copy of the table will also be available from the USPTO upon request and payment of the fee set forth in 37 CFR 1.19(b)(3).

---

Signed and Sealed this

Sixth Day of October, 2009

David J. Kappos
*Director of the United States Patent and Trademark Office*